(12) United States Patent
Kline et al.

(10) Patent No.: US 8,375,533 B2
(45) Date of Patent: Feb. 19, 2013

(54) FASTENING SYSTEM HAVING MULTIPLE ENGAGEMENT ORIENTATIONS

(75) Inventors: Mark James Kline, Okeana, OH (US); Ronald Joseph Zink, II, Blue Ash, OH (US); Jeromy Thomas Raycheck, Lebanon, OH (US); George Henry Leal, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 201 days.

(21) Appl. No.: 12/871,355

(22) Filed: Aug. 30, 2010

(65) Prior Publication Data

US 2011/0054435 A1 Mar. 3, 2011

Related U.S. Application Data

(63) Continuation of application No. 11/240,838, filed on Sep. 30, 2005, now Pat. No. 7,799,006.

(51) Int. Cl.
*A44B 1/00* (2006.01)

(52) U.S. Cl. .......................................................... 24/701

(58) Field of Classification Search .................. 24/698.1, 24/700–702

See application file for complete search history.

(56) References Cited

U.S. PATENT DOCUMENTS

| | | | |
|---|---|---|---|
| 3,860,003 A | 1/1975 | Buell | |
| 3,911,173 A | 10/1975 | Sprague, Jr. | |
| 3,929,135 A | 12/1975 | Thompson | |
| 4,315,508 A * | 2/1982 | Bolick ........................... | 604/371 |
| 4,324,246 A | 4/1982 | Mullane et al. | |
| 4,342,314 A | 8/1982 | Radel et al. | |
| 4,463,045 A | 7/1984 | Ahr et al. | |
| 4,502,192 A | 3/1985 | Hess | |
| 4,515,595 A | 5/1985 | Kievit et al. | |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |
| 4,673,402 A | 6/1987 | Weisman et al. | |
| 4,695,278 A | 9/1987 | Lawson | |
| 4,713,864 A | 12/1987 | Hess | |
| 4,785,996 A | 11/1988 | Ziecker et al. | |
| 4,834,735 A | 5/1989 | Alemany et al. | |
| 4,842,666 A | 6/1989 | Werenicz | |
| 4,882,321 A | 11/1989 | Maurer et al. | |
| 4,892,536 A | 1/1990 | Desmarais et al. | |
| 4,909,803 A | 3/1990 | Aziz et al. | |
| 4,940,464 A | 7/1990 | Van Gompel et al. | |
| 4,990,147 A | 2/1991 | Freeland | |
| 5,006,394 A | 4/1991 | Baird | |
| 5,037,416 A | 8/1991 | Allen et al. | |
| 5,092,861 A | 3/1992 | Nomura et al. | |
| 5,137,537 A | 8/1992 | Herron et al. | |

(Continued)

FOREIGN PATENT DOCUMENTS

WO  WO-95/16746 A1  6/1995
WO  WO-95/24173 A2  9/1995

*Primary Examiner* — James Brittain
(74) *Attorney, Agent, or Firm* — Andrew J. Mueller; William E. Gallagher

(57) ABSTRACT

A fastening system has a first fastening member and a second fastening member. The first member has a retaining element and a substrate element. The retaining element includes a proximal edge and a distal edge and is attached to the substrate element along a line of attachment. The second fastening member has an inboard portion, an outboard portion, and an elongated opening disposed between the inboard and outboard portions. The elongated opening is configured such that at least part of the retaining element is capable of passing through the elongated opening when the retaining element is in a first orientation and when the retaining element is in a second orientation.

12 Claims, 12 Drawing Sheets

U.S. PATENT DOCUMENTS

| | | |
|---|---|---|
| 5,147,345 A | 9/1992 | Young et al. |
| 5,151,092 A | 9/1992 | Buell et al. |
| 5,221,274 A | 6/1993 | Buell et al. |
| 5,246,433 A | 9/1993 | Hasse et al. |
| 5,260,345 A | 11/1993 | Desmarais et al. |
| 5,269,775 A | 12/1993 | Freeland et al. |
| 5,342,338 A | 8/1994 | Roe |
| 5,387,207 A | 2/1995 | Dyer et al. |
| 5,518,801 A | 5/1996 | Chappell et al. |
| 5,569,234 A | 10/1996 | Buell et al. |
| 5,571,096 A | 11/1996 | Dobrin et al. |
| 5,609,587 A | 3/1997 | Roe |
| 5,625,222 A | 4/1997 | Yoneda et al. |
| 5,635,191 A | 6/1997 | Roe et al. |
| 5,643,588 A | 7/1997 | Roe et al. |
| 5,865,823 A | 2/1999 | Curro |
| 5,897,545 A | 4/1999 | Kline et al. |
| 5,938,648 A | 8/1999 | Lavon et al. |
| 5,957,908 A | 9/1999 | Kline et al. |
| 5,968,025 A | 10/1999 | Roe et al. |
| 6,120,487 A | 9/2000 | Ashton |
| 6,120,489 A | 9/2000 | Johnson et al. |
| 6,423,049 B1 | 7/2002 | Tominaga et al. |
| 6,432,098 B1 | 8/2002 | Kline et al. |
| 6,689,116 B1 * | 2/2004 | Ekdahl et al. .................. 604/391 |
| 6,715,188 B1 * | 4/2004 | Jackson et al. ............... 24/698.1 |
| 6,716,441 B1 | 4/2004 | Osborne et al. |
| 6,880,211 B2 | 4/2005 | Jackson et al. |
| 2003/0233082 A1 | 12/2003 | Kline et al. |
| 2007/0149938 A1 | 6/2007 | Ruiz et al. |

* cited by examiner

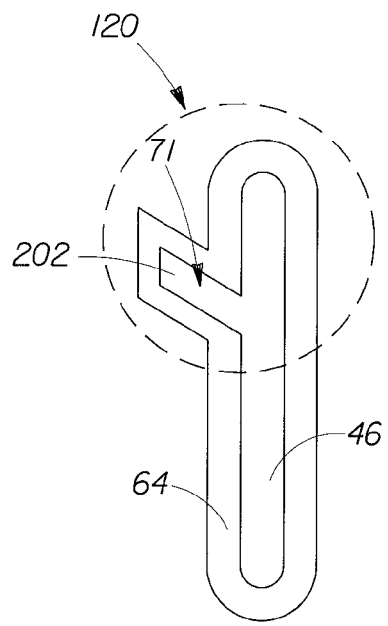
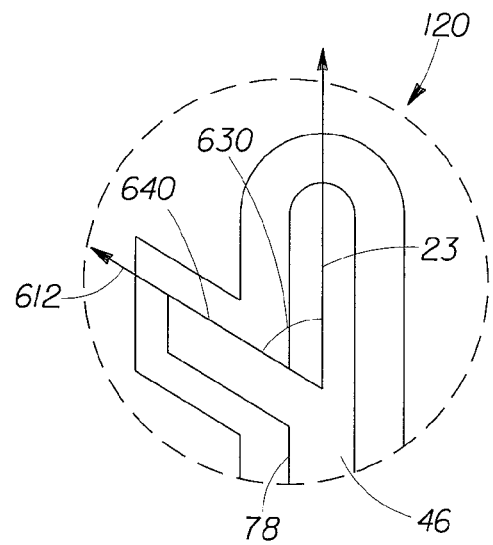
Fig. 4A
Fig. 4B
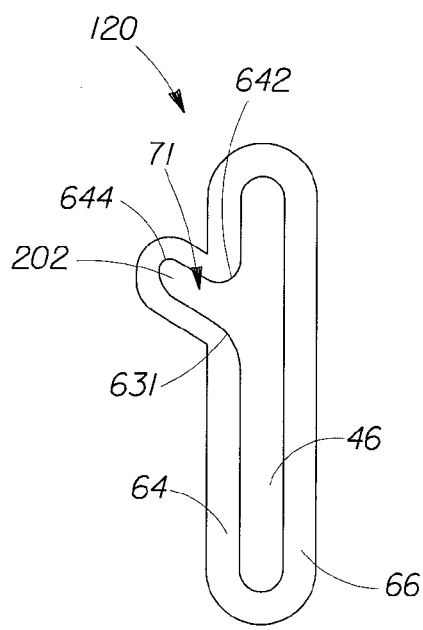
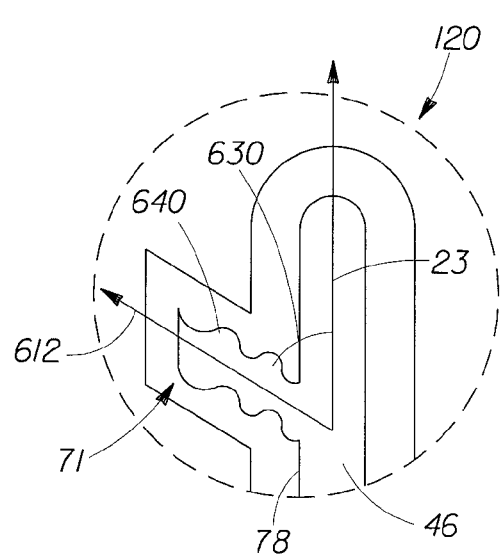
Fig. 4D
Fig. 4C

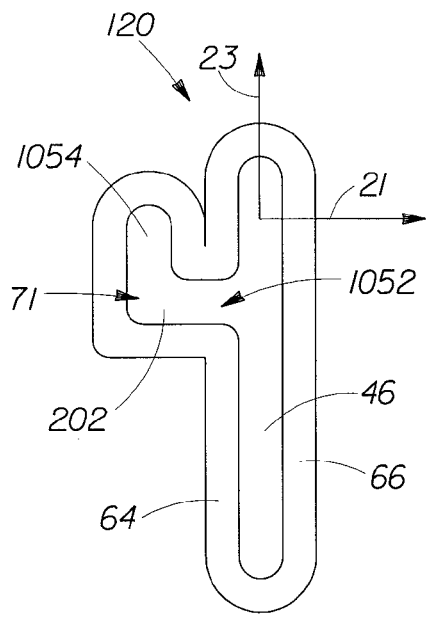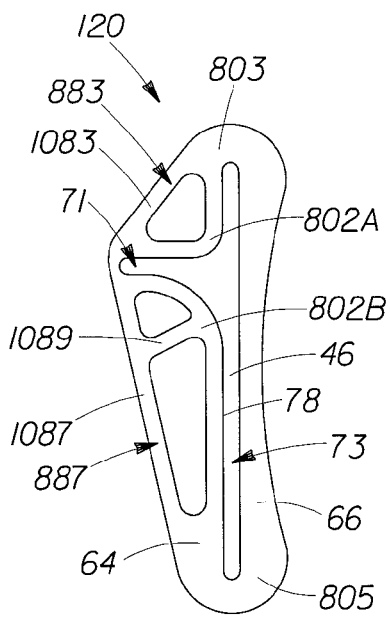
Fig. 5 Fig. 6
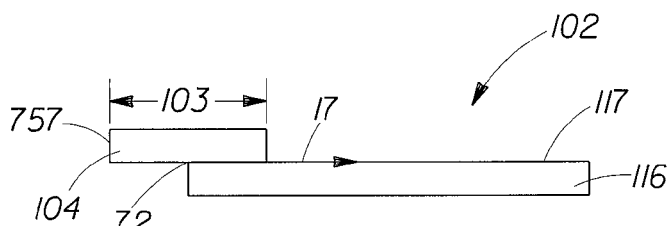
Fig. 7A
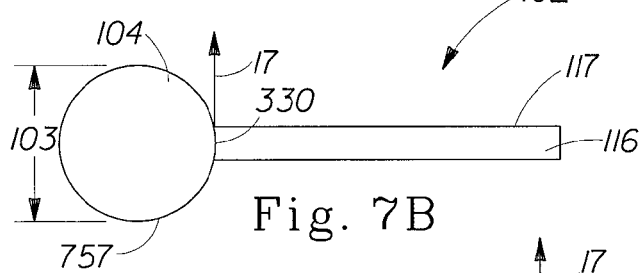
Fig. 7B
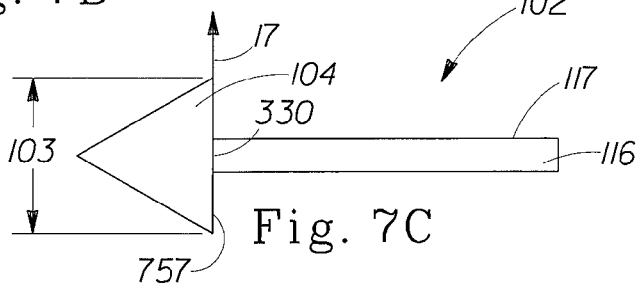
Fig. 7C

FASTENING SYSTEM HAVING MULTIPLE ENGAGEMENT ORIENTATIONS

CROSS REFERENCE TO RELATED APPLICATION

This application is a continuation of application Ser. No. 11/240,838, filed Sep. 30, 2005 now U.S. Pat. No. 7,799,006, the substance of which is incorporated herein by reference.

FIELD OF THE INVENTION

The present invention pertains to fastening systems. The present invention also pertains to disposable absorbent articles which utilize fastening systems.

BACKGROUND OF THE INVENTION

Fastening systems are widely used on a variety of articles, examples of which include disposable absorbent articles. Some fastening systems can create non-refastenable attachments between materials. In many cases these non-refastenable attachments cannot be unattached and effectively refastened after being unattached. Other fastening systems create refastenable attachments between materials which can be unattached and subsequently refastened.

Examples of refastenable fastening systems may include hook and loop type fastening systems, hook and hook type fastening systems, as well as some adhesive type fastening systems. Typically these fastening systems include fastening elements such as an engaging component and a landing component. In general, the engaging component and the landing component have to be aligned in a face-to-face relationship before fastening because misalignment of the engaging component and the landing component can result in poor fastening system performance. In addition, some refastenable fastening systems, e.g. adhesive type fastening systems, can become easily contaminated by foreign material which can reduce the performance of the fastening system.

Another example of a refastenable fastening system is a macrofastener type fastening system. Macrofasteners are an alternative type of fastening system which can aid in achieving proper alignment of the fastening elements being connected. Moreover, macrofasteners are generally contamination-proof.

Examples of macrofastener type fastening systems include snaps, buttons, and hook and eye type fastening systems. Unfortunately, the fastening elements of these macrofastener fastening systems, in a fastened state, generally allow rotation about a single point which can be problematic in some applications. In order to reduce the ability to rotate about the single point, multiple fastening elements may be required. Because multiple fastening elements may be required to reduce the ability to rotate about the single point, these macrofastener fastening systems may be considered non-ideal for many applications including absorbent articles.

Another example of a macrofastener type fastening system is the tab and slot type fastening system. Tab and slot fastening systems typically include a tab member and a slot member. The tab member typically includes a tab element attached to a substrate element, and the slot member includes a slot which is configured to receive the tab element.

In general, the tab and slot fastening system can be fastened when the tab element is in either a first orientation or a second orientation. In order to fasten the tab and slot fastening system while the tab member is in the first orientation, a proximal edge of the tab element can be inserted and passed through the slot, and subsequently, a distal edge of the tab element can be passed through the slot.

In order to fasten the tab and slot fastening system while the tab member is in the second orientation, the tab element generally is passed through the slot such that the proximal edge and the distal edge pass through the slot contemporaneously. Once the tab element passes through the slot, the tab element is generally pivoted such that part of the proximal edge of the tab element engages an outboard portion of the slot member, and part of the distal edge of the tab element engages an inboard portion of the slot member. However, because the slot is typically narrow in width, the tab element typically has to be pivoted relative to the slot such that the tab element is generally parallel to the substrate element as the tab element passes through the slot.

Unfortunately, fastening the tab and slot fastening system when the tab member is in the second orientation can require a caregiver or a wearer to perform awkward hand movements. These awkward hand movements can cause ergonomic stress to the caregiver or the wearer performing these awkward hand movements.

In addition, in some applications, the performance of these awkward hand movements can become increasingly difficult. For example, an infant wearer of a disposable absorbent article can be moving around while donning the disposable absorbent article. Given the sometimes unpredictable nature of the movements of the wearer, the difficulty in performing these awkward hand movements can increase.

Consequently, it would be advantageous to provide a versatile fastening system which facilitates the fastening of its fastening elements by allowing at least one of the fastening elements to be oriented in more than one orientation during fastening. It would also be advantageous to provide a versatile fastening system which reduces the likelihood of the performance of awkward hand movements to fasten the fastening elements of the versatile fastening system.

SUMMARY OF THE INVENTION

Fastening systems constructed in accordance with the present invention comprise a first fastening member and a second fastening member. The first fastening member comprises a substrate element and a retaining element. The retaining element is attached to the substrate element along a line of attachment which has a line of attachment length greater than about 25% of a retaining element length. The retaining element length is generally parallel to a first longitudinal axis. The retaining element also has a retaining element width which is generally parallel to a lateral axis. The lateral axis is generally perpendicular to the first longitudinal axis.

The second fastening member includes an inboard portion and an outboard portion which, in conjunction, define an elongated opening in the second fastening member. The elongated opening includes a second longitudinal axis. The elongated opening is configured such that at least part of the retaining element is capable of passing through the elongated opening when the retaining element is in a first orientation and when the retaining element is in a second orientation, thereby fastening the first fastening member and the second fastening member. When the retaining element begins to pass through the elongated opening of the second fastening member in the second orientation an orientation angle between the lateral axis of the retaining element and the second longitudinal axis of the elongated opening is greater than about 0 degrees and less than about 180 degrees.

In another embodiment of the present invention, a fastening system may include all of the features of the fastening system described above. Additionally, this fastening system may be configured such that the retaining element is capable of moving about 2 mm along an x-axis, a y-axis, or a z-axis, with respect to the second fastening member without unfastening the first fastening member from the second fastening member.

In yet another embodiment of the present invention, a fastening system may comprise a first fastening member and a second fastening member. The first fastening member may include a substrate element and a retaining element, wherein the retaining element is attached to the substrate element along a line of attachment. The retaining element has a retaining element length.

The second fastening member includes an inboard portion and an outboard portion which, in conjunction, define an elongated opening in the second fastening member. The elongated opening includes a longitudinal axis and has an elongated opening length. The elongated opening further includes a longitudinal region and an intersecting region, wherein the longitudinal region includes a longitudinal region width and the intersecting region includes an intersection region width. The intersecting region width is greater than the longitudinal region width, and at least part of the retaining element is capable of passing through the elongated opening and engaging the outboard portion of the second fastening member, thereby fastening the first fastening member and the second fastening member. Additionally, the retaining element length is greater than about 25% of the elongated opening length.

In yet another embodiment, a disposable absorbent article constructed in accordance with the present invention may comprise a first waist region, a second waist region, a crotch region disposed between the first and second waist regions; a first waist edge and a second waist edge; and a first longitudinal edge and a second longitudinal edge. The disposable absorbent article further comprises a topsheet, a backsheet attached to at least a portion of the topsheet, and an absorbent core disposed between the topsheet and the backsheet.

The disposable absorbent article further comprises a tab and slot fastening system including a tab member and a slot member. The tab member includes a tab element having a first lip section and a second lip section. The first lip section may comprise a proximal edge and the second lip section may comprise a distal edge.

The tab member also includes a substrate element attached to the tab element along a line of attachment, wherein the line of attachment is disposed between the proximal edge and the distal edge. The substrate element is attached to the disposable absorbent article in the second waist region.

The tab and slot fastening system also includes a slot member which is disposed in the first waist region of the disposable absorbent article. The slot member comprises an inboard portion, an outboard portion, and a slot disposed between the inboard portion and the outboard portion. The slot comprises a longitudinal region and an intersecting region, wherein the longitudinal region includes a longitudinal region width and the intersecting region includes an intersection region width. The intersecting region width is greater than the longitudinal region width.

In a fastened state, at least part of the proximal edge can overlap the outboard portion of the slot member, thereby fastening the first waist region and the second waist region of the disposable absorbent article.

BRIEF DESCRIPTION OF THE DRAWINGS

FIG. 4A is a plan view showing another embodiment of a second fastening member constructed in accordance with the present invention.

FIG. 4B is a close up view showing part of the second fastening member of FIG. 4A.

FIG. 4C is a close up view showing part of another embodiment of a second fastening member constructed in accordance with the present invention.

FIG. 4D is a plan view showing another embodiment of a second fastening member constructed in accordance with the present invention.

FIG. 5 is a plan view showing another embodiment of a second fastening member constructed in accordance with the present invention.

FIG. 6 is a plan view showing another embodiment of a second fastening member constructed in accordance with the present invention.

FIGS. 7A-7G are elevation views showing a side of other embodiments of first fastening members constructed in accordance with the present invention.

DETAILED DESCRIPTION OF THE INVENTION

Figure 1A:
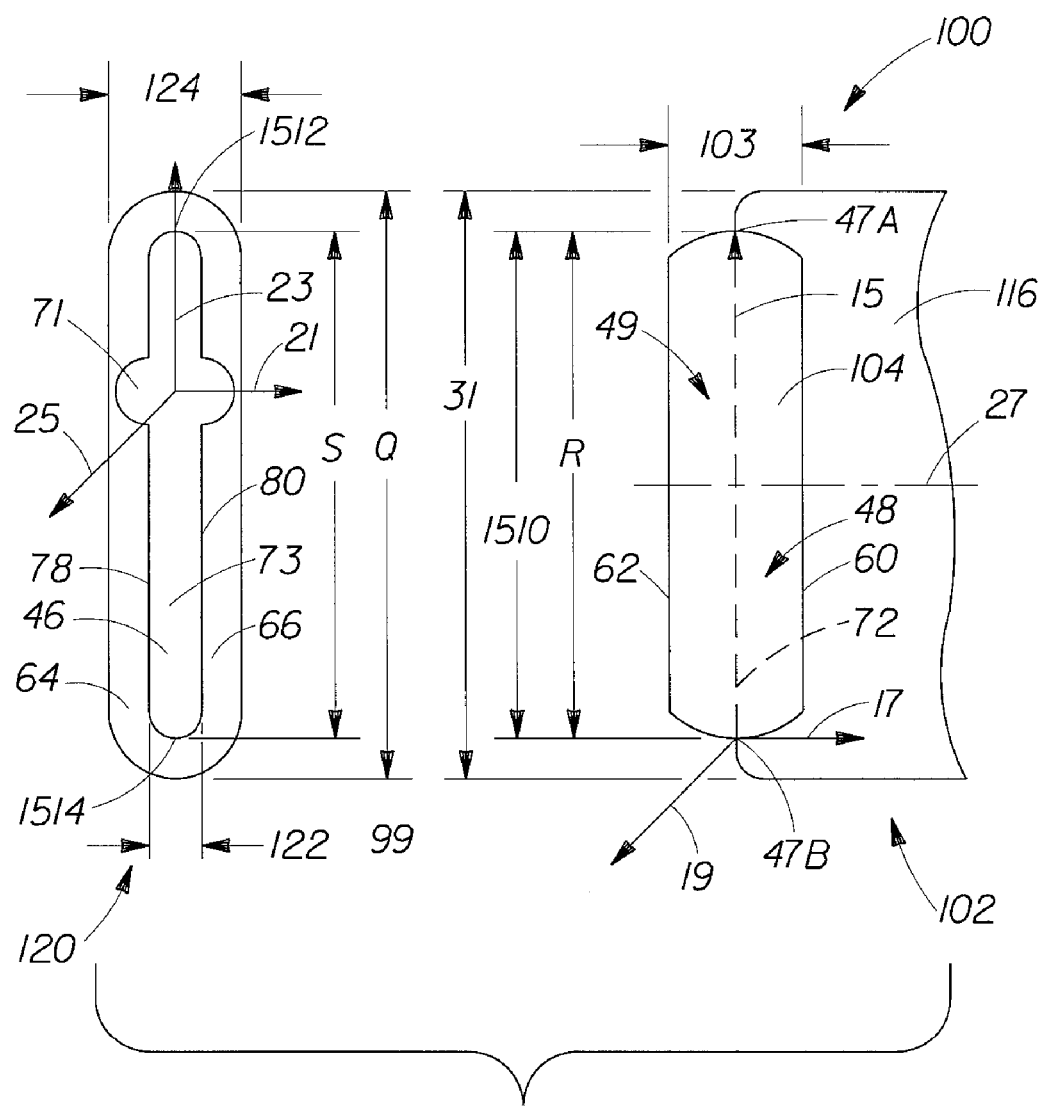
FIG. 1A is a plan view showing a fastening system constructed in accordance with the present invention.

Definitions:

As used herein, the terms "absorbent article" and "article" refer to a wearable device that absorbs and/or contains liquid and, more specifically, refer to devices that are placed against or in proximity to the body of the wearer to absorb and contain the various exudates discharged from the body. Suitable examples include diapers, training pants, refastenable pants, pull-on garments, adult incontinence products and feminine care products such as sanitary napkins. Furthermore, the terms "absorbent article" and "article" include a "disposable absorbent article" which is intended to be discarded and not laundered or otherwise restored after no more than ten uses, preferably after no more than five uses, and most preferably after a single use (although certain components may be recycled, reused, or composted).

The term "attached" refers to elements being connected or united by fastening, adhering, bonding, etc. by any method suitable for the elements being fastened, secured, or joined, together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently. The term "attached" includes elements which are integrally formed from another element.

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

As used herein "elastically extensible" refers to characteristics of extensible materials that have the ability to return to approximately their original dimensions after a force that extended the extensible material is removed. Herein, any material or element described as "extensible" may also be "elastically extensible" unless otherwise provided.

The term "longitudinal" is used herein to refer to a direction which is generally parallel to the longest edge of an element except where otherwise noted. In the context of diapers, a "longitudinal" direction runs substantially perpendicular from a waist edge to an opposing waist edge of the article and generally parallel to the maximum linear dimension of the article. Directions within ±45 degrees of the longitudinal direction are considered to be "longitudinal".

The term "lateral" refers to a direction running generally perpendicular to and in the same plane as the "longitudinal" direction. In the context of diapers, a "lateral" direction runs from one longitudinal edge of the article to an opposing longitudinal edge of the article. Directions within ±45 degrees of the lateral direction are considered to be "lateral".

The term "transverse" refers to a direction which is generally perpendicular to the plane of the longitudinal and lateral directions. Directions within ±45 degrees of the transverse direction are considered to be "transverse".

The terms "pant", "training pant", "closed diaper", "prefastened diaper", and "pull-on diaper", as used herein, refer to disposable garments designed for infants, incontinent individuals, etc., wherein the disposable garments can have a waist opening and a pair of leg openings. A pant can be configured such that the pant has a closed waist and closed leg openings prior to being donned on the wearer, or the pant can be configured such that the waist is closed and the leg openings formed while on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082 A1.

Description:

The fastening systems of the present invention can facilitate the engagement of its fastening elements by allowing at least one of the fastening elements to be oriented in more than one orientation during fastening. A fastening system constructed in accordance with the present invention can also reduce the likelihood that awkward hand movements need to be performed for fastening the fastening elements of the fastening system.

As shown in FIG. 1A, a fastening system 100 constructed in accordance with the present invention may comprise a first fastening member 102 and a second fastening member 120. The first fastening member 102 comprises a retaining element 104 and a substrate element 116. The retaining element 104 can be an elongated element having a retaining element length R and can be attached to the substrate element 116 along a line of attachment 72. The retaining element length R can be defined by the maximum linear distance between a first longitudinal end 47A and a second longitudinal end 47B of the retaining element 104, which is generally parallel to a first longitudinal axis 15. The retaining element 104 has a retaining element width 103 which can be the maximum linear distance between two outermost points on a periphery 757 (shown in FIGS. 7A-7G) of the retaining element 104, wherein the lateral distance is generally parallel to a first lateral axis 17. As shown, in some embodiments, the retaining element width 103 can be the distance between a proximal edge 60 and a distal edge 62 of the retaining element 104. The first lateral axis 17 is discussed further in regard to FIGS. 7A-7G.

The first longitudinal axis 15 can be drawn between two longitudinally outermost points on the line of attachment 72. As shown, in some embodiments, the first longitudinal axis 15 and the line of attachment 72 can be collinear, but the first longitudinal axis 15 and the line of attachment 72 are not required to be. In some embodiments, the first longitudinal end 47A and the second longitudinal end 47B can correspond to the two longitudinally outermost points on the line of attachment 72. In some embodiments, the first longitudinal axis 15 can be generally parallel to the distal edge 62 and/or the proximal edge 60. The first lateral axis 17 can be generally perpendicular to the first longitudinal axis 15. Similarly, a first transverse axis 19 can be generally perpendicular to both the first longitudinal axis 15 and the first lateral axis 17 and extend out toward the viewer of FIG. 1A.

The retaining element 104 may further comprise a first lip section 48 and a second lip section 49. The first lip section 48 includes the proximal edge 60, and the second lip section 49 includes the distal edge 62. The first lip section 48 comprises part of the retaining element 104 which is not attached to the substrate element 116 to which the retaining element 104 is attached. The second lip section 49 may comprise part of the retaining element 104 which is attached to the substrate element 116.

As shown, the retaining element 104 can be attached to the substrate element 116 along the line of attachment 72 such that the first lip section 48 of the retaining element 104 extends laterally inward over at least part of the substrate element 116. Although the line of attachment 72 is shown generally parallel to the proximal edge 60, the line of attachment 72 can also be at any angle thereto. The line of attachment 72 can be any suitable shape. For example, in some embodiments, the line of attachment 72 may be non-linear. In other embodiments, the line of attachment 72 may be C-shaped, D-shaped, V-shaped, etc., or at any angle relative to a longitudinal centerline 27 of the substrate element 116.

The line of attachment 72 can be disposed between the proximal edge 60 and the distal edge 62 of the first lip section 48 and the second lip section 49. Also, embodiments where the line of attachment 72 is disposed on the distal edge 62 are contemplated.

A line of attachment length 1510, when compared to the retaining element length R, can vary greatly. For example, in some embodiments, the line of attachment length 1510 can extend from about 25% to about 100% of the retaining element length R or any individual number within the range. In other embodiments, the line of attachment length 1510 can extend to about 25% of the retaining element length R. In yet other embodiments, the line of attachment length 1510 can extend to about 50% of the retaining element length R. As shown, in yet other embodiments, the line of attachment length 1510 can extend to about 100% of the retaining element length R.

Similarly, the retaining element length R can vary greatly with respect to a substrate element length 31 adjacent to the line of attachment 72. As shown, the substrate element length 31 adjacent to the line of attachment 72 generally runs perpendicular to the longitudinal centerline 27 of the substrate element 116.

In some embodiments, the retaining element length R can be greater than about 25% of the substrate element length 31 adjacent to the line of attachment 72 or any individual number above 25%. In other embodiments, the retaining element length R can be greater than or equal to about 50% of the substrate element length 31 adjacent to the line of attachment 72. In yet other embodiments, the retaining element length R can be greater than or equal to about 75% of the substrate element length 31 adjacent to the line of attachment 72. In yet other embodiments, the retaining element length R can be greater than or equal to about 100% of the substrate element length 31 adjacent to the line of attachment 72.

As discussed previously, the fastening system 100 of the present invention further comprises the second fastening member 120. The second fastening member 120 may comprise an inboard portion 64, an outboard portion 66, and an elongated opening 46 disposed between the inboard portion 64 and the outboard portion 66. The inboard portion 64 may include an inboard edge 78 which can define part of the elongated opening 46. Similarly, the outboard portion 66 may include an outboard edge 80 which can also define part of the elongated opening 46.

The second fastening member 120 and the elongated opening 46 can have lengths Q and S, respectively. The elongated opening length S can be defined by the maximum linear distance between a first opening longitudinal end 1512 and a second opening longitudinal end 1514. The length S of the elongated opening 46 can by any suitable length. For example, in some embodiments the length S of the elongated opening 46 can be less than the length Q of the second fastening member 120. Additionally, in some embodiments, the length S of the elongated opening 46 can be greater than or equal to the retaining element length R. Where the S is greater than or equal to the retaining element length R, the retaining element 104 can be easily passed through the elongated opening 46 without undue bending or deformation of either component, in some embodiments, when the retaining element 104 is oriented in a first orientation and inserted into the elongated opening 46. However, in other embodiments, the length S of the elongated opening 46 can be less than the retaining element length R. Where the length S is less than the retaining element length R, the retaining element 104 can be passed through the elongated opening 46 when the retaining element 104 is oriented in a second orientation and inserted into the elongated opening 46. In embodiments where S is less than the retaining element length R, the retaining element 104 and/or the second fastening member 120 may comprise a compressible material which allows the retaining element 104 to pass through the elongated opening 46 in the first orientation and the second orientation. A discussion of the materials for the retaining element 104 and for the second fastening member 120 is provided hereafter. Similarly, both the first and the second orientations are discussed hereafter.

In other embodiments, the retaining element length R can be greater than or equal to about 25% of the length S or any individual number greater than 25%. In other embodiments, the retaining element length R can be greater than or equal to about 50% of the length S. In yet other embodiments, the retaining element length R can be greater than or equal to about 75% of the length S. In yet other embodiments, the retaining element length R can be greater than or equal to about 100% of the length S.

The elongated opening 46 further comprises a second lateral axis 21, a second longitudinal axis 23, and a second transverse axis 25. In some embodiments, the second longitudinal axis 23 can generally run parallel to the inboard edge 78 and/or the outboard edge 80 of the second fastening member 120. The second lateral axis 21 can generally run perpendicular to the second longitudinal axis 23. The second transverse axis 25 can generally run perpendicular to the second lateral axis 21 and the second longitudinal axis 23 and can extend toward the viewer of FIG. 1A. The second longitudinal axis is discussed further hereafter.

The elongated opening 46 may further comprise a longitudinal region 73, and an intersecting region 71. The longitudinal region 73 includes a longitudinal region width 122, and the intersecting region 71 includes an intersecting region width 124. Suitable elongated openings 46 may also include slots or slits and may further include loops under which retaining elements may be fed and interlocked. Other exemplary elongated openings 46 are discussed in U.S. Pat. No. 6,432,098.

The intersecting region width 124 can be greater than the longitudinal region width 122. The longitudinal region width 122 can correspond to the maximum linear distance, generally parallel to the second lateral axis 21, between the inboard edge 78 and the outboard edge 80 of the second fastening member 120. In some embodiments, the longitudinal region width 122 can be about 0.5 mm to about 6 mm or any individual number within the range. In other embodiments, the longitudinal region width 122 can be less than about 50% of the retaining element width 103. In yet other embodiments, the longitudinal region width 122 can be less than or equal to about 25% of the retaining element width 103. In yet other embodiments, the longitudinal region width 122 can be at least greater than or equal to a depth 190 (shown in FIG. 1C) of the retaining element 104 such that the retaining element 104 can pass through the elongated opening 46 when the retaining element 104 is in the first orientation without having to compress the retaining element 104 in a direction generally parallel to the first transverse axis 19.

Figure 1B:
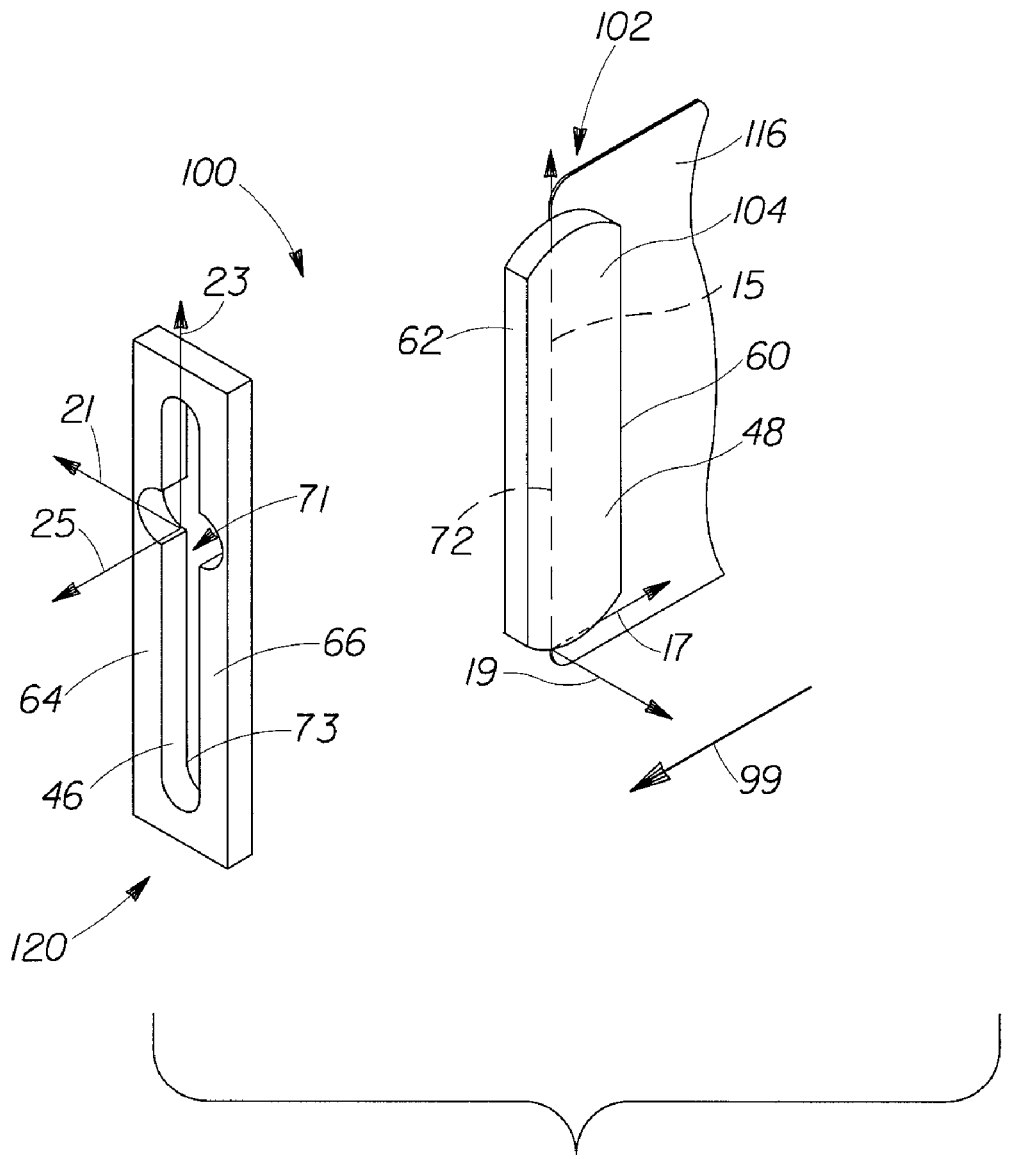
FIG. 1B is an isometric view showing the fastening system of FIG. 1A, wherein a first fastening member is in a first orientation.

As shown in FIG. 1B, the fastening system 100 of the present invention can be fastened when the first fastening member 102 is in the first orientation, and, as mentioned previously, when in the second orientation. The first fastening member 102 can be oriented in the first orientation when the first longitudinal axis 15 of the retaining element 104 is generally perpendicular to an engagement direction 99, and the first longitudinal axis 15 is generally parallel to the second longitudinal axis 23 of the second fastening member 120. The first fastening member 102 and the second fastening member 120 can be fastened together by passing the retaining element 104 completely through the elongated opening 46. Note that during fastening, the second fastening member 120 is typically arranged such that the second transverse axis 25 is generally parallel to the engagement direction 99.

During fastening, when the retaining element 104 is in the first orientation, the proximal edge 60 can pass through the elongated opening 46 before the distal edge 62, or the distal edge 62 can pass through the elongated opening 46 before the proximal edge 60. While the retaining element 104 passes through the elongated opening 46, the first longitudinal axis 15 of the retaining element 104 and the second longitudinal axis 23 of the second fastening member 120 can be generally parallel. Once the retaining element 104 passes through the elongated opening 46, the retaining element 104 can pivot with respect to the substrate element 116 such that the first lip section 48 can lift away from the substrate element 116. When the first lip section 48 is lifted from the substrate element 116, the first lip section 48 can engage the outboard portion 66 of the second fastening member 120, thereby fastening the first fastening member 102 and the second fastening member 120.

The fastening system 100 of the present invention offers advantages when the retaining element 104 is in the first orientation. For example, when the retaining element 104 is in the first orientation, the intersecting region width 124 (see FIG. 1A) of the intersecting region 71 can allow a caregiver or a wearer to more easily grab the retaining element 104 as the retaining element 104 passes through the elongated opening 46, thereby facilitating the fastening of the first fastening member 102 and the second fastening member 120, in some embodiments.

Figure 1C:
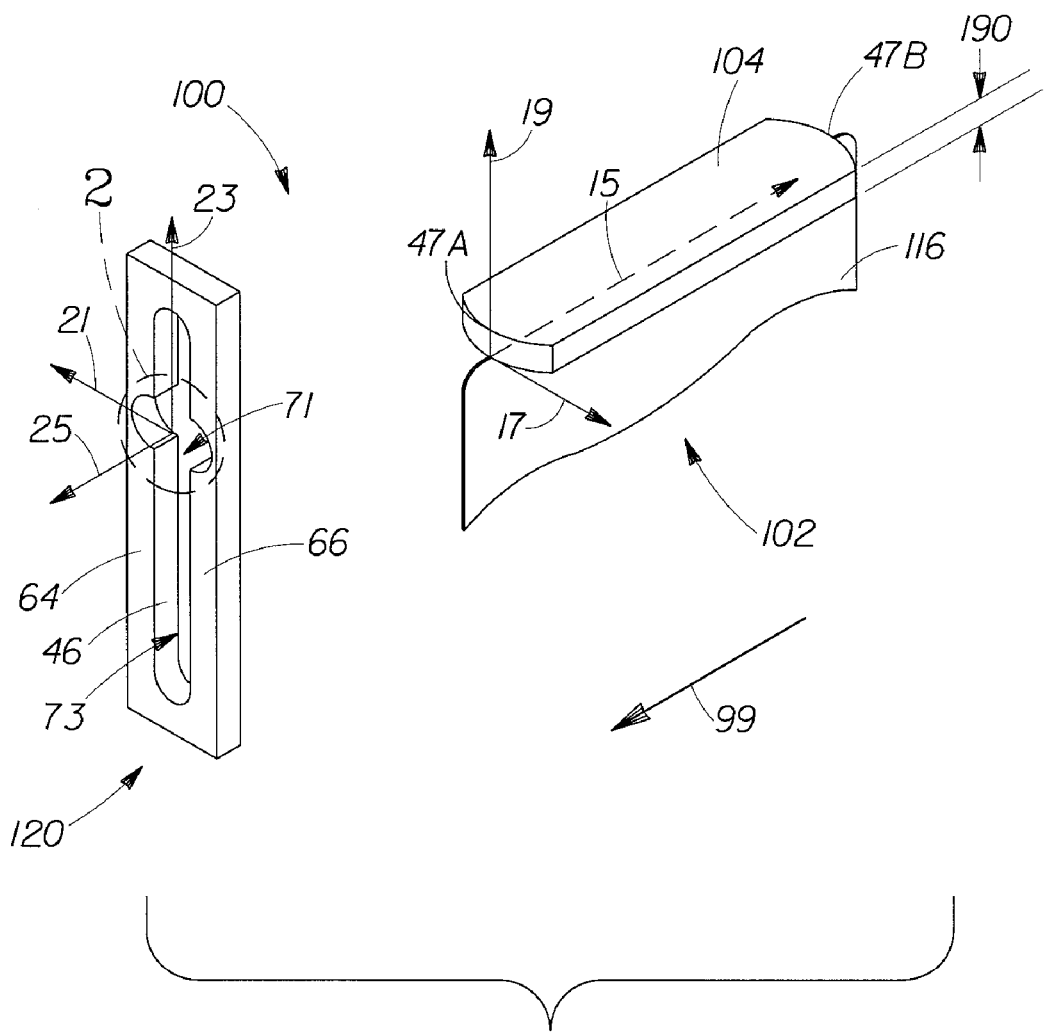
FIG. 1C is an isometric view showing the fastening system of FIG. 1A, wherein the first fastening member is in a second orientation.

As shown in FIG. 1C, the fastening system 100 can also be fastened when the retaining element 104 is oriented in the second orientation. The retaining element 104 can be in the second orientation when the first longitudinal axis 15 of the retaining element 104 is generally parallel to the engagement direction 99. Similar to the first orientation, the first fastening member 102 and the second fastening member 120 can be fastened together by passing the retaining element 104 completely through the elongated opening 46. However, to begin engagement of the first fastening member 102 and the second fastening member 120, when the first fastening member 102 is in the second orientation, the first longitudinal end 47A or the second longitudinal end 47B of the retaining element 104 can be inserted into the elongated opening 46. In this configuration, the first longitudinal axis 15 of the retaining element 104 and the second longitudinal axis 23 of the second fastening member 120 can be generally perpendicular. Once part of the retaining element 104 passes through the elongated opening 46, the retaining element 104 can be pulled in a direction generally parallel to the second longitudinal axis 23 of the second fastening member 120 such that the first lip section 48 (see FIGS. 1A and 1B) can engage the outboard portion 66 of the second fastening member 120, thereby fastening the first fastening member 102 and the second fastening member 120.

As shown, the retaining element 104 may comprise the depth 190 which is generally parallel to the first transverse axis 19. In some embodiments, the first transverse axis 19 can be generally parallel to the second longitudinal axis 23 as the retaining element 104 begins to pass through the elongated opening 46. Additionally, in some embodiments, the first lateral axis 17 can be generally perpendicular to the second longitudinal axis 23 as the retaining element 104 begins to pass through the elongated opening 46. The orientation of the first, lateral axis 17 with respect to the second longitudinal axis 23 is discussed further in regard to FIGS. 1D and 1E.

Another advantage of the fastening system 100 of the present invention is that when in the second orientation, a force used to pull the retaining element 104 through the elongated opening 46 typically does not cause deformation of the retaining element 104. In contrast, when in the first orientation, for example, in order to fasten the fastening system 100, forces can be applied to the first fastening member 102 which are generally perpendicular to the first longitudinal axis 15 of the retaining element 104. These applied forces can cause necking forces in the substrate element 116 which are generally parallel to the first longitudinal axis 15 of the retaining element 104 and can be compressive in nature. These compressive forces can cause the retaining element 104 to deform adjacent to its longitudinal ends 47A and 47B. However, when in the second orientation, the applied forces are generally parallel to the first longitudinal axis 15 of the retaining element 104. In the second orientation, any necking forces that are created are typically parallel to the first longitudinal axis 15 of the retaining element 104 and are non-compressive. Therefore, the retaining element 104 typically experiences less deformation when being fastened while in the second orientation.

Figure 1D:
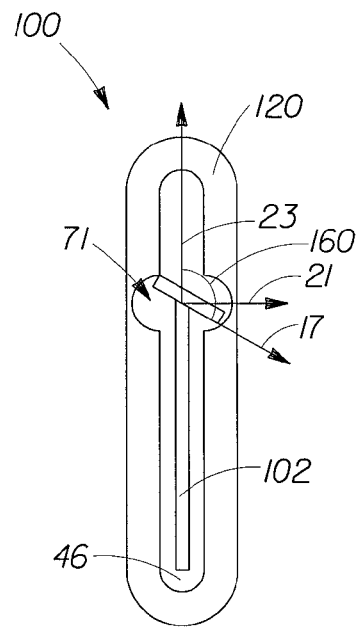
FIG. 1D is an isometric view showing the first fastening member of FIG. 1A with a coordinate system of a second fastening member superimposed on the first fastening member.
Figure 1E:
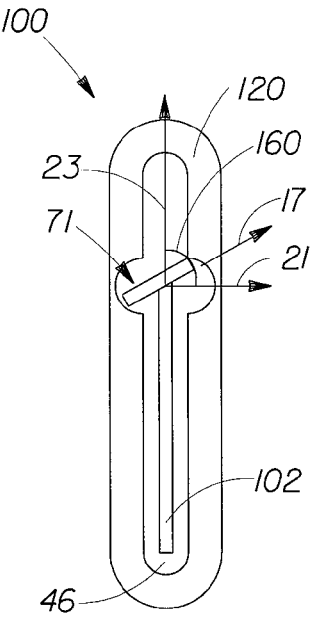
FIG. 1E is an elevation view showing a side of the first fastening member of FIG. 1A with the coordinate system of the second fastening member superimposed on the first fastening member.

As shown in FIGS. 1D and 1E, in order to facilitate explanation, the first fastening member 102 is shown beginning to pass through the second fastening member 120. FIGS. 1D and 1E illustrate the orientation of the retaining element 104 with respect to the orientation of the elongated opening 46 when the retaining element 104 begins to pass through the elongated opening 46. As shown in FIGS. 1D and 1E, depending on the configuration of the intersecting region 71 (configurations of the intersecting region 71 are discussed hereafter), the first lateral axis 17 can be oriented at various angles with respect to the second longitudinal axis 23 of the second fastening member 120 as the retaining element 104 begins to pass through the elongated opening 46. For example, as shown in FIG. 1D, in some embodiments, the retaining element 104 can begin to pass through the second fastening member 120 at an orientation angle 160 between the first lateral axis 17 and the second longitudinal axis 23 which is greater than 90 degrees. In contrast, in another example, as shown in FIG. 1E, the orientation angle 160 can be less than 90 degrees.

In some embodiments, the orientation angle 160, between the first lateral axis 17 of the retaining element 104 and the second longitudinal axis 23 of the second fastening member 120 can be greater than about 0 degrees to less than about 180 degrees or any individual number within the range. In other embodiments, the orientation angle 160 can be from greater than or equal to about 10 degrees to less than or equal to about 170 degrees. In yet other embodiments, the orientation angle 160 can be from greater than about 0 degrees to less than or equal to about 90 degrees. In yet other embodiments, the orientation angle 160 can be greater than or equal to about 45 degrees to less than or equal to about 90 degrees. In yet other embodiments, the orientation angle 160 can range from about 90 degrees to about 135 degrees.

Advantageously, the range of the orientation angle 160 can reduce the likelihood that awkward hand movements will have to be performed while fastening the first fastening member 102 and the second fastening member 120. For example, while fastening the first fastening member 102 and the second fastening member 120, a caregiver or a wearer can rotate the retaining element 104 into a position which facilitates fastening and reduces the likelihood of the performance of awkward hand movements during fastening.

Additionally, the fastening system 100 of the present invention facilitates engagement of the first fastening member 102 and the second fastening member 120 because the first fastening member 102 can engage the second fastening member 120 from the first orientation and from the second orientation. This flexibility allows the caregiver or wearer to choose whichever orientation is easiest to accomplish the fastening of the first fastening member 102 and the second fastening member 120.

Figure 2:
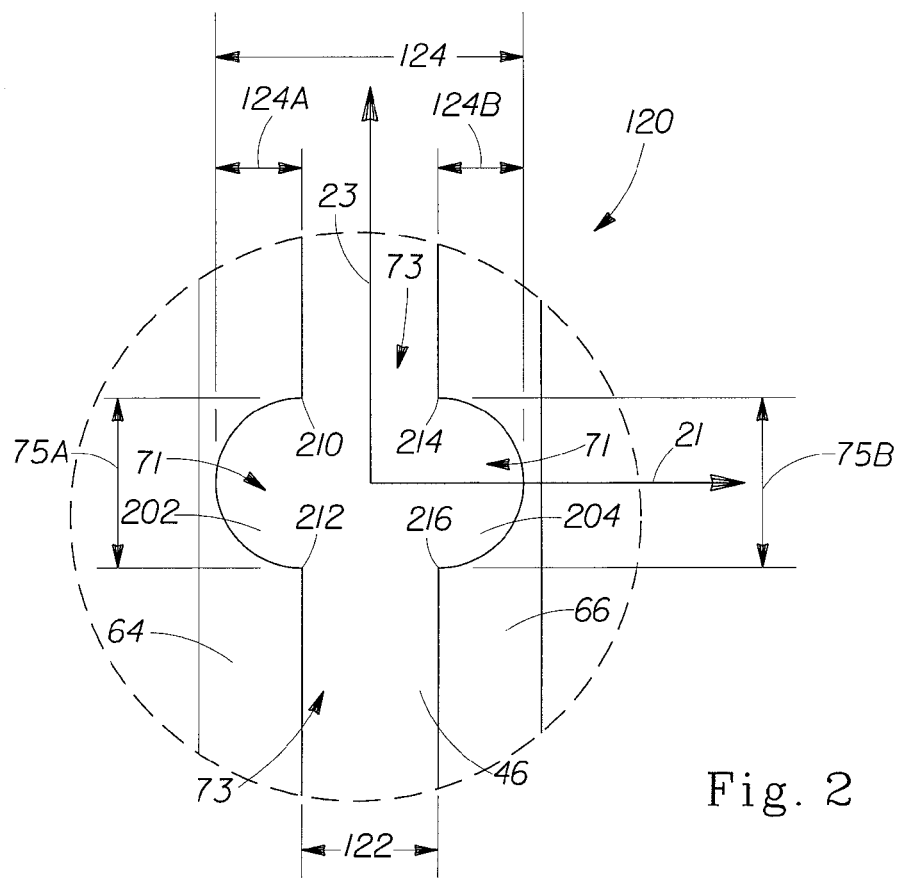
FIG. 2 is a close up view showing part of a second fastening member of the fastening system of FIG. 1A.

As shown in FIG. 2, in some embodiments, the intersecting region 71 of the elongated opening 46 may comprise a first area 202 and a second area 204. The first area 202 can extend outward from the elongated opening 46 and into the inboard portion 64. The second area 204 can extend outward from the elongated opening 46 and into the outboard portion 66. As discussed hereafter, embodiments are contemplated where the intersecting region 71 comprises either the first area 202 or the second area 204, but not both.

The first area 202 can have a first area width 124A, and the second area 204 can have a second area width 124B. The first area width 124A can be the maximum linear distance, generally parallel to the second lateral axis 21, between the inboard edge 78 and a point furthest away from the inboard edge 78 in the first area 202. Similarly, the second area width 124B can be the maximum linear distance, generally parallel to the second lateral axis 21, between the outboard edge 80 and a point furthest away from the outboard edge 80 in the second area 204.

In some embodiments, the intersecting region width 124 can be equal to cumulative widths of the first area width 124A, the second area width 124B, and the longitudinal region width 122. In other embodiments, the intersecting region width 124 can be greater than or equal to about 50% of the retaining element width 103 (shown in FIG. 1A) or any individual number above 50%. In other embodiments, the intersecting region width 124 can be greater than or equal to about 75% of the retaining element width 103 (shown in FIG. 1A). In yet other embodiments, the intersecting region width 124 can be greater than or equal to about 100% of the retaining element width 103 (shown in FIG. 1A).

As shown, in some embodiments, the first area width 124A can be about equal to the second area width 124B. However, in other embodiments, the first area width 124A can be less than the second area width 124B. In yet other embodiments, the first area width 124A can be greater than the second area width 124B. In yet other embodiments, either the first area width 124A or the second area width 124B can be equal to zero.

The first area 202 further comprises a first area length 75A, and the second area 204 further comprises a second area length 75B. The first area length 75A can be the maximum longitudinal distance, generally parallel to the second longitudinal axis 23, between a first point of intersection 210 and a second point of intersection 212. Both the first point of intersection 210 and the second point of intersection 212 can represent the intersection between the longitudinal region 73 and the first area 202 of the intersecting region 71. Similarly, the second area length 75B can be the maximum longitudinal distance, generally parallel to the second longitudinal axis 23, between a third point of intersection 214 and the fourth point of intersection 216. Both the third point of intersection 214 and the fourth point of intersection 216 can represent the intersection between the longitudinal region 73 and the second area 204 of the intersecting region 71.

Each of the first area length 75A and the second area length 75B is less than the length S (shown in FIG. 1A) of the elongated opening 46. Each of the first area length 75A and the second area length 75B of the first and second areas 202 and 204 can be any suitable length. For example, in some embodiments, the first area length 75A can be less than or equal to about 90% of the length S (shown in FIG. 1A) of the elongated opening 46 or any individual number less than 90%. In other embodiments, the first area length 75A can be less than about 75% of the length S (shown in FIG. 1A) of the elongated opening 46. In other embodiments, the first area length 75A can be less than about 50% of the length S (shown in FIG. 1A) of the elongated opening 46. In yet other embodiments, the first area length 75A can be less than about 25% of the length S (shown in FIG. 1A) of the elongated opening 46. In yet other embodiments, the first area length 75A can be less than about 10% of the length S (shown in FIG. 1A) of the elongated opening 46. In yet other embodiments, the first area length 75A can be greater than or about equal to the depth 190 (shown in FIG. 1C) of the retaining element 104. The second area length 75B can vary to the same extent as described above in regard to the first area length 75A. Also, while the first area length 75A and the second area length 75B can be equal to one another, they are not required to be.

In embodiments where the first area width 124A or the second area width 124B are equal to zero, their respective lengths 75A or 75B can also be equal to zero. For example, the intersecting region 71 may comprise only the second area 204. In these embodiments, because the intersecting region 71 does not include the first area 202, the first area width 124A and the first area length 75A are equal to zero.

The first area 202 and the second area 204 of the intersecting region 71 can be any suitable shape known in the art. Examples of suitable shapes for use in the first area 202 and the second area 204 are discussed hereafter in regard to FIGS. 3A-3E and 4A-4D.

Figure 3A:
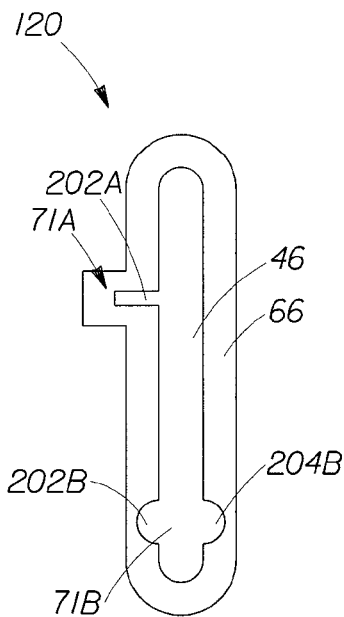
FIGS. 3A-3E are plan views showing other embodiments of second fastening members constructed in accordance with the present invention.

As shown in FIG. 3A, in some embodiments, the second fastening member 120 may comprise a plurality of intersecting regions. As shown, in some embodiments, the elongated opening 46 may comprise a first intersecting region 71A which includes a first area 202A. The first area 202A can extend outward from the elongated opening 46 into the inboard portion 64 and comprise a rectangular shape. The elongated opening 46 may further comprise a second intersecting region 71B which includes a first area 202B and a second area 204B. The first area 202B can extend outward from the elongated opening 46 into the inboard portion 64, and the second area 204B can extend outward from the elongated opening 46 into the outboard portion 66. As shown, in some embodiments, the first area 202B and the second area 204B may comprise an arcuate shape.

Figure 3B:
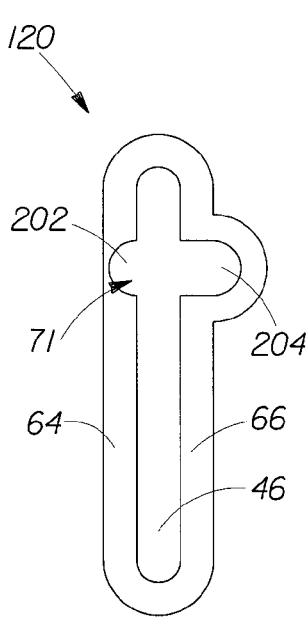

As shown in FIG. 3B, in some embodiments, the second fastening member 120 may comprise the intersecting region 71 which has the first area 202 and the second area 204. The first area 202 can extend outward from elongated opening 46 into the inboard portion 64, and the second area 204 can extend outward from the elongated opening 46 into the outboard portion 66. As discussed previously, the first area 202 and the second area 204 can extend outward from the elongated opening 46 by the same amount, but the first area 202 and the second area 204 are not required to extend outboard from the elongated opening 46 by the same amount.

Figure 3C:
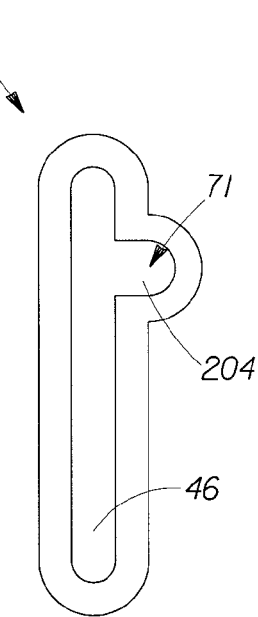

As shown in FIG. 3C, in some embodiments, the intersecting region 71 can include only the second area 204. In embodiments where the intersecting region 71 does not include the first area, the first area width 124A and the first area length 75A (shown in FIG. 2) can both be equal to zero.

Figure 3D:
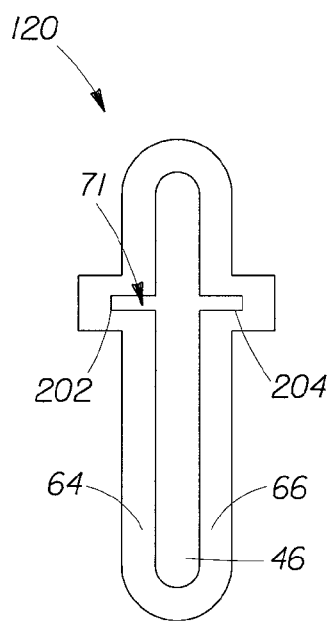

As shown in FIG. 3D, in some embodiments, the intersecting region 71 may comprise the first area 202 and the second area 204. The first area 202 can extend outward from the elongated opening 46 into the inboard portion 64, and the second area 204 can extend outward from the elongated opening 46 into the outboard portion 66. As shown the first area 202 and/or the second area 204 may comprise a rectangular shape.

Figure 3E:
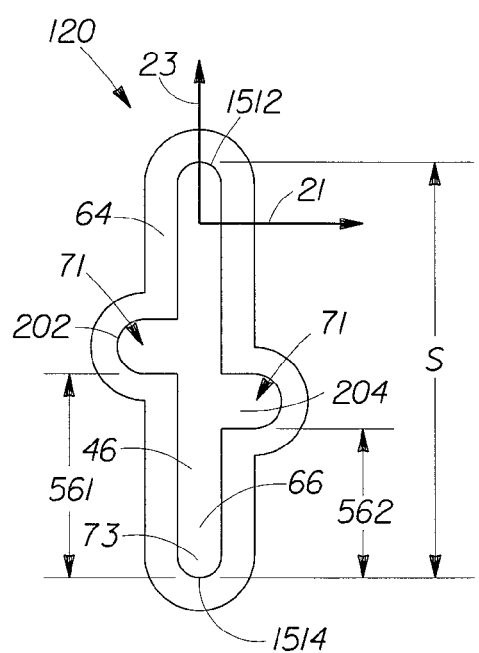

As shown in FIG. 3E, the second fastening member 120 may comprise the intersecting region 71 which includes the first area 202 and the second area 204. The first area 202 can extend outward from the elongated opening 46 into the inboard portion 64 at a first height 561. Similarly, the second area 204 can extend outward from the elongated opening 46 into the outboard portion 66 at a second height 562.

The first height 561 and the second height 562 are measured from the second opening longitudinal end 1514 which represents a height of zero. The first height 561 can be defined by the distance between the second point of intersection 212 (shown in FIG. 2) where first area 202 intersects the longitudinal region 73 and the second opening longitudinal end 1514. Similarly, the second height 562 can be defined by the distance between the fourth point of intersection 216 (shown in FIG. 2) where the second area 204 intersects the longitudinal region 73 and the second opening longitudinal end 1514.

As shown, in some embodiments, the first area 202 can be longitudinally displaced from the second area 204. For example, in some embodiments, the first height 561 can be greater than the second height 562. In other embodiments, the first height 561 can be less than the second height 562.

The intersecting region 71 of the second fastening member 120 can be displaced anywhere along the elongated opening 46. For example, the first height 561 and the second height 562 can be equal to about the length S of the elongated opening 46 such that the intersecting region 71 is disposed adjacent to the first opening longitudinal end 1512 of the elongated opening 46. In another example, the first height 561 and the second height 562 can be equal to zero such that the intersecting region 71 is disposed adjacent to the second opening longitudinal end 1514 of the elongated opening 46. In yet another example, the first height 561 and/or the second height 562 can be greater than about 10% of the elongated opening length S or any individual number greater than 10%. In yet another example, the first height 561 and/or the second height 562 can be equal to about 10% to about 90% of the elongated opening length S. In yet another example, the first height 561 and/or the second height 562 can be equal to about 50% to about 90% of the elongated opening length S. In yet another example, the first height 561 and/or the second height 562 can be equal to about 15% to about 30% of the elongated opening length S. In yet another example, the first height 561 and/or the second height 562 can be equal to about 55% to about 70% of the elongated opening length S.

All of the second fastening members discussed heretofore have included an intersecting region which extended outward from the elongated opening 46 into the inboard portion 64, into the outboard portion 66, or both, generally parallel to the second lateral axis 21. However, the intersecting region 71 can extend outward from the elongated opening 46 into the inboard portion 64, into the outboard portion 66, or both at any angle as shown in FIGS. 4A-4D.

As shown in FIGS. 4A and 4B, the second fastening member 120 may comprise the intersecting region 71 which includes the first area 202 which extends outward from the elongated opening 46 into the inboard portion 64. As shown in FIG. 4B, the elongated opening 46 may comprise the second longitudinal axis 23 and an angular axis 612. The intersection of the second longitudinal axis 23 and the angular axis 612 can form an intersecting region angle 630 which is discussed hereafter.

As shown, in some embodiments, where the inboard edge 78 is generally straight, the second longitudinal axis 23 may be generally parallel to the inboard edge 78. Similarly, in some embodiments, where a first edge 640 of the first area 202 is generally straight, the angular axis 612 may coincide with the first edge 640. However, embodiments are contemplated where the angular axis 612 does not coincide with the first edge 640. FIG. 4C provides an example of the non-coincidental nature of the first edge 640 and the angular axis 612.

As shown in FIG. 4C, the angular axis 612 does not have to be coincidental with the first edge 640 of the intersecting region 71. As shown, the angular axis 612 can be drawn between the longitudinally inwardmost points of the first edge 640. Similarly, although not shown, the second longitudinal axis 23 can be drawn between the laterally inwardmost points of the inboard edge 78.

The intersecting region angle 630 between the second longitudinal axis 23 and the angular axis 612 can vary greatly. For example, in some embodiments, the intersecting region angle 630 can be greater than about 0 degrees to less than about 180 degrees or any individual number within this range. In other embodiments, the intersecting region angle 630 can be greater than about 0 degrees and less than about 120 degrees. In other embodiments, the intersecting region angle 630 can be greater than about 0 degrees and less than about 90 degrees. In yet other embodiments, the intersecting region angle 630 can be greater than about 0 degrees and less than about 45 degrees. In yet other embodiments, the intersecting region angle 630 can be greater than about 45 degrees to less than about 90 degrees. In yet other embodiments, the intersecting region angle 630 can be greater than or equal to about 90 degrees and less than or equal to about 135 degrees.

In conjunction with, or independently from the first area 202, the intersecting region 71 may include a second area which extends outward from the elongated opening 46 into the outboard portion 66 at an angle which is similar to the intersecting region angle 630. For example, in some embodiments, the second area can extend outward into the outboard portion 66 at an angle greater than about 0° to less than about 180° or any individual number within the range.

As shown in FIG. 4D, the second fastening member 120 may comprise the intersecting region 71. However, the second fastening member 120 may further comprise rounded transition regions 631, 642, and 644. These rounded transition regions 631, 642, and 644, can facilitate both the engagement and disengagement of the retaining element 104 (shown in FIGS. 1A-1E) from the second fastening member 120. For example, in embodiments where the retaining element 104 comprises a cloth-like material, the rounded transitions can greatly reduce the likelihood that the retaining element 104 will snag as the retaining element 104 (shown in FIGS. 1A-1E) passes through the elongated opening 46. Examples of suitable materials for constructing the retaining element are discussed hereafter.

As discussed previously, the second fastening member 120 may further comprise the intersecting region 71 which includes a plurality of areas which extend outward from the elongated opening 46 into the inboard portion 64 and/or into the outboard portion 66. However, embodiments are contemplated where the first area 202 and/or the second area 204 (shown in FIGS. 2 and 3B-3E) are subdivided into a plurality of pieces. An example of such a second fastening member is shown in FIG. 5.

As shown in FIG. 5, the second fastening member 120 may comprise the intersecting region 71 which includes the first area 202. The first area 202 may comprise an initial piece 1052 which extends laterally outward, in some embodiments, from the elongated opening 46 into the inboard portion 64. The laterally outward extension can be generally parallel to the second lateral axis 21. The first area 202 may further comprise an end piece 1054 which extends longitudinally outward, in some embodiments, from the initial piece 1052. The longitudinally outward extension can be generally parallel to the second longitudinal axis 23. In conjunction with or independently from the first area 202, a second area comprising a plurality of pieces can extend outward from the elongated opening 46 into the outboard portion 66.

The initial piece 1052 and the end piece 1054 can be oriented in any suitable configuration. For example, the initial piece 1052 may extend outward from the elongated opening 46 at any angle described above in regard to FIGS. 4A-4D. Similarly the end piece 1054 can extend outward from the initial piece 1052 at any suitable angle. The initial piece 1052 and the end piece 1054 can be configured in a variety of manners. For example, the configuration of the initial piece 1052 and the end piece 1054 can facilitate the engagement of T-shaped retaining elements, L-shaped retaining elements, W-shaped retaining elements, and the like, with the second fastening member 120.

For certain uses of the fastening system of the present invention, the first fastening member and/or the second fastening member may comprise reinforcement members. For example, a second fastening member utilized in disposable absorbent articles may comprise materials which are soft and compliant and therefore non-irritating to a wearer's skin. However, in order to support expected use forces, the second fastening member may need to be reinforced in certain locations.

As shown in FIG. 6, the second fastening member 120 may comprise the elongated opening 46 including the intersecting region 71. The elongated opening 46 can be defined by the inboard portion 64 and the outboard portion 66. The inboard portion 64 may comprise a first reinforcement zone 883 and/or a second reinforcement zone 887.

The first reinforcement zone 883 can provide support to a first interface 802A between the longitudinal region 73 and the intersecting region 71 of the elongated opening 46 as well as to a first end section 803 of the second fastening member 120. In some embodiments, the first reinforcement zone 883 may comprise a first reinforcement member 1083 which extends from the first end section 803 of the second fastening member 120 to the intersecting region 71.

The first reinforcement member 1083 can distribute forces applied to the first interface 802A and the first end section 803 of the second fastening member 120 about the first reinforcement zone 883, thereby reducing the likelihood that the first interface 802A and the first end section 803 of the second fastening member 120 deflect to such an extent as to complicate fastening or as to allow unintentional unfastening of the retaining element 104 (shown in FIGS. 1A-1E) from the second fastening member 120.

Similarly, the second reinforcement zone 887 can provide support for a second interface 802B between the longitudinal region 73 and the intersecting region 71 of the elongated opening 46. The second reinforcement zone 887 may comprise a second reinforcement member 1087 which extends from a second end section 805 of the second fastening member 120 to the intersecting region 71 of the elongated opening 46. Additionally, the second reinforcement zone 887, in some embodiments, may further comprise a third reinforcement member 1089 which extends from the second reinforcement member 1087 to the inboard edge 78 of the second fastening member 120. The second reinforcement member 1087 and the third reinforcement member 1089 can distribute forces applied to the second interface 802B and the second end section 805 of the second fastening member 120, thereby reducing the likelihood that the second interface 802B and the second end section 805 of the second fastening member 120 deflect to such an extent as to complicate fastening or as to allow unintentional unfastening of the retaining element from the second fastening member 120.

The reinforcement zones 883 and 887 may utilize any suitable means of reinforcing the second fastening member 120 and reducing deflection of the first interface 802A, the second interface 802B, the first end section 803, and the second end section 805. For example, in some embodiments, the reinforcement members 1083, 1087, and 1089, may comprise a plurality of beams. In other embodiments, the first reinforcement members 1083 can be a continuous material which extends from the first reinforcement member 1083 to the first interface 802A. The second reinforcement member 1087 and the third reinforcement member 1089 can be configured in a similar manner to that of the first reinforcement member 1083.

As discussed heretofore, the first area 202 and the second area 204 of the elongated opening 46 of the second fastening member 120 may comprise any suitable shape known in the art. Additionally and also discussed previously, the intersecting region 71 can be configured in a variety of ways with respect to the longitudinal region 73 of the elongated opening 46. However, the shape of the intersecting region 71 as well as the orientation of the intersecting region 71 with respect to the longitudinal region 73 can impact the shape of a retaining element.

A retaining element, constructed in accordance with the present invention, may comprise any suitable shape known in the art. For example, the retaining element may comprise a circular shape, a rectangular shape, a triangular shape, a trapezoidal shape, a rhomboidal shape, the shape of a parallelogram, a polygonal shape, the like, or any combination thereof. Examples of suitable retaining element shapes are shown in FIGS. 7A-7G. The examples of FIGS. 7A-7G show retaining elements from a viewpoint which is generally parallel to the first longitudinal axis 15 (shown in FIGS. 1A-1C).

As shown in FIGS. 7A-7G, the first fastening member 102 of the present invention comprises the retaining element 104 which is attached to the substrate element 116 along the line of attachment 72. Also, as shown, the retaining element width 103 is generally parallel to the first lateral axis 17 and is the maximum lateral distance between two outermost points on the periphery 757 of the retaining element 104. The configuration of the first lateral axis 17 is discussed below. In the embodiments of the first fastening member 102 shown in FIGS. 7A-7G, the retaining element can be attached to the end 330 of the substrate element 116 or the surface 117 of the substrate element 116.

As shown in FIG. 7A, in some embodiments, the retaining element 104 can be relatively thin and flat and disposed on a surface 117 of the substrate element 116. For example, the retaining element 104 can be a tab as described in U.S. Pat. No. 6,432,098 and in U.S. Patent Application Publication No. 2003/0233082. Also, as shown, in embodiments where the retaining element 104 is attached to the surface 117 of the substrate element 116, the first lateral axis 17 is generally parallel to the surface 117 of the substrate element 116 at the line of attachment 72.

In contrast, as shown in FIGS. 7B-7G, where the retaining element 104 is attached to an end 330 of the substrate element 116, the first lateral axis 17 is generally perpendicular to the surface 117 of the substrate element 116. The position of the first lateral axis 17 with respect to the surface 117 of the substrate element 116 is established when the substrate element 116 is on a flat horizontal surface.

Figure 7D:
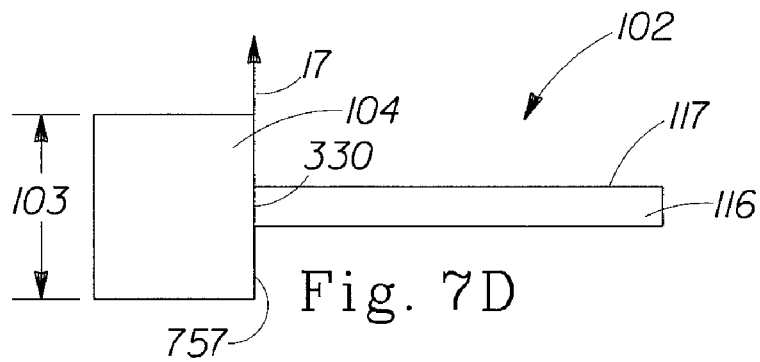
Figure 7E:
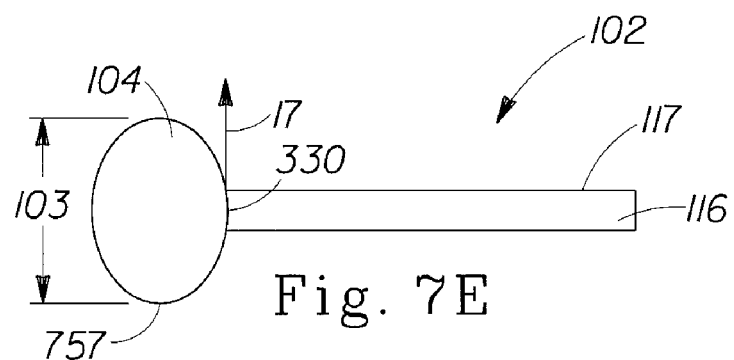
Figure 7F:
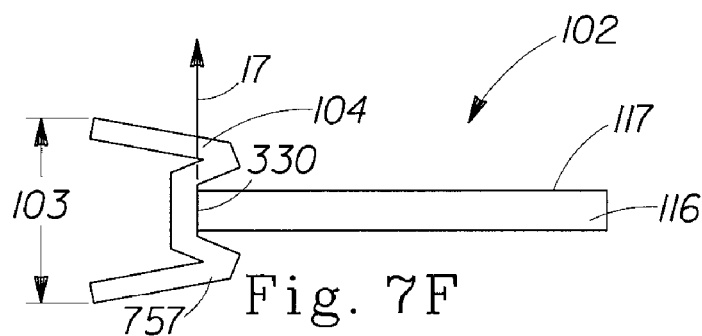
Figure 7G:
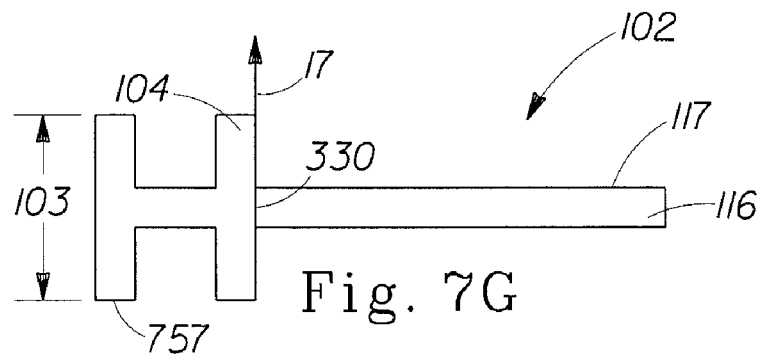

As shown in FIG. 7B, in some embodiments, the retaining element 104 may comprise a generally circular shape having the retaining element width 103 which corresponds to a diameter of the generally circular shape. As shown in FIG. 7C, in other embodiments, the retaining element 104 may comprise a generally triangular shape having the retaining element width 103 which corresponds to a length of a base of the generally triangular shape. As shown in FIG. 7D, in some embodiments, the retaining element 104 may comprise a generally rectangular shape having the retaining element width 103 which corresponds to a distance between opposite sides of the generally rectangular shape. As shown in FIG. 7E, in other embodiments, the retaining element 104 may comprise a generally elliptical shape having the retaining element width 103 which corresponds to a major axis of the generally elliptical shape. As shown in FIG. 7F, in other embodiments, the retaining element 104 may comprise a generally W-shaped component having the retaining element width 103 which corresponds to a distance between two outermost points on the generally W-shaped component. As shown in FIG. 7G, in some embodiments, the retaining element 104 may comprise a generally rail shaped component. In embodiments where the retaining element 104 comprises a generally rail shaped component, the first fastening member 102 and the second fastening member 120 (shown in FIGS. 1A-1E 2, 3A-3E, 4A-4C, 5, and 6) can be fastened together when part of the retaining element 104 engages the outboard portion 66 (shown in FIGS. 1A-1C, 2, 3A-3E, 4A-4D, 5, and 6) of the second fastening member 120.

Regardless of the shape utilized, the retaining element width 103 should allow at least part of the retaining element 104 to engage the outboard portion 66 (shown in FIGS. 1A-1C, 2, 3A-3E, 4A-4D, 5, and 6) of the second fastening member 120 (shown in FIGS. 1A-1E, 2, 3A-3E, 4A-4D, 5, and 6). In some embodiments, the retaining element width 103 of the retaining element 104 should allow the retaining element 104 to engage the outboard portion 66 (shown in FIGS. 1A-1C, 2, 3A-3E, 4A-4D, 5, and 6) and the inboard portion 64 (shown in FIGS. 1A-1C, 2, 3A-3E, 4A-4D, 5, and 6) of the second fastening member 120.

The first fastening members of FIGS. 7A through 7G can be described as "multiplane hinge" fastening members. A first fastening member which is a multiplane hinged fastening member can comprise a retaining element which can be a separate element attached to the substrate element. In other multiplane embodiments, the substrate element can be folded upon itself such that the retaining element is integral to the substrate element. In yet other embodiments, retaining elements can be integrally formed from a substrate element. Examples of integrally formed retaining elements are discussed below in regard to FIGS. 8A-8C.

Figure 8A:
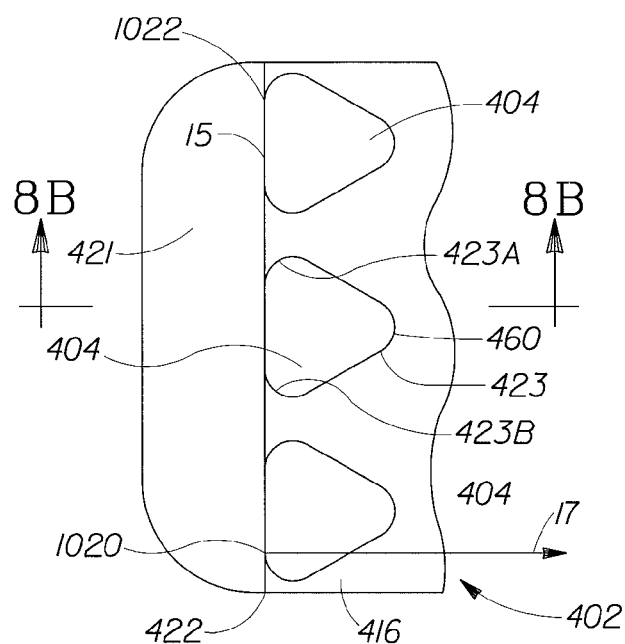
FIG. 8A is a plan view showing an alternative embodiment of a first fastening member constructed in accordance with the present invention.
Figure 8B:
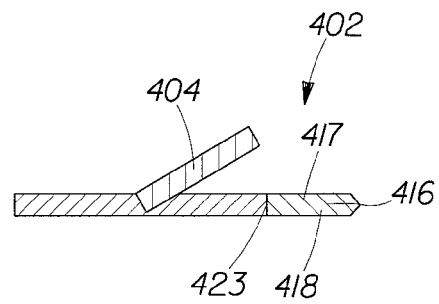
FIG. 8B is a cross sectional view showing the first fastening member of FIG. 8A as seen through line 8B-8B.
Figure 8C:
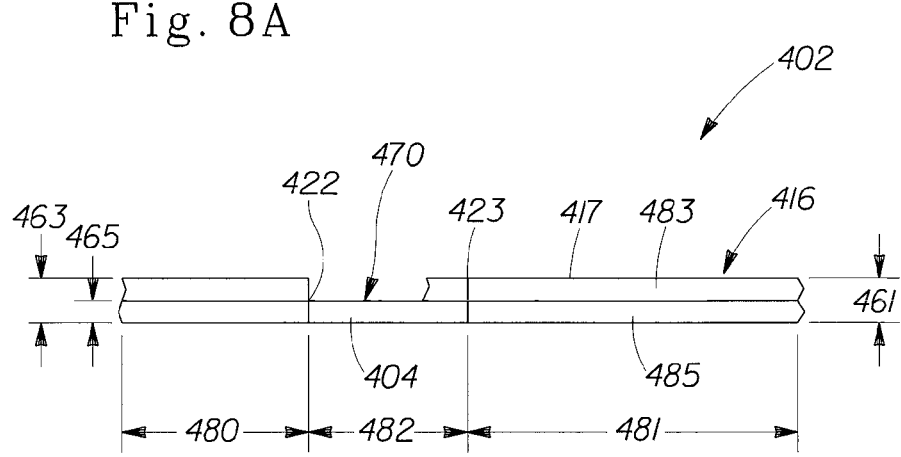
FIG. 8C is a cross sectional view showing another embodiment of a first fastening member.

As shown in FIGS. 8A-8C, a first fastening member 402, constructed in accordance with the present invention, can be a single plane hinged fastening member. In some embodiments, first fastening member 402 can be configured such that no part of the first fastening member 402 overhangs another part of the first fastening member 402. Other exemplary single plane hinged fastening members are described in U.S. Patent Application Publication No. 2003/0233082A1 and in U.S. Pat. No. 6,880,211.

As shown in FIG. 8A, the first fastening member 402 may comprise a substrate element 416 having a single plane hinge line 422 and plurality of retaining elements 404. The single plane hinge line 422 for the first fastening member 402 can be similar to the line of attachment 72 (shown in FIGS. 1A, 1B, and 7A-7G). For example, the retaining elements 404 of the first fastening member 402 can pivot about the single plane hinge line 422 in some embodiments. The first longitudinal axis 15 can be drawn between two longitudinally outermost points 1020 and 1022 of the retaining elements 404 along the single plane hinge line 422. The first lateral axis 17 can be generally perpendicular to the first longitudinal axis 15.

As shown there are three retaining elements 404; however, embodiments having fewer than three or more than three are contemplated. In embodiments comprising more than one retaining element 404, each retaining element 404 may be identically shaped, or alternatively, at least one of the retaining elements 404 may be a different shape than another retaining element 404.

The retaining elements 404 can be formed, for example, by cutting the substrate element 416 along at least one cut line 423 to form at least one proximal edge 460. As shown, the cut line 423 can follow a path which begins at a first point 423A and ends at a second point 423B. The path from first point 423A to the second point 4238 can form a portion of the single plane hinge line 422. The cut line 423 may take any path provided that the cut line 423 results in at least a portion of the retaining element 404 being capable of overlapping an outboard portion of a second fastening member when the fastening system is engaged. When the first fastening member 402 is engaged with a second fastening member, the retaining elements 404 may be bent out of the plane of the first fastening member 402 generally along the single plane hinge line 422 such that retaining elements 404 overlap the outboard portion of the second fastening member. Furthermore, when the first fastening member 402 is engaged with the second fastening member, a distal portion 421 of the first fastening member 402 can overlap an inboard portion of the second fastening member.

As shown in FIG. 8B, the cut line 423 may extend from the first surface 417 through a second surface 418 of the substrate element 416 such that any resulting retaining elements 404 do not overlap any portion of the substrate element 416. Alternatively, the cut line 423 may extend from the first surface 417 through only part of the substrate element 416 such that the resulting retaining elements 404 overlap the substrate element 416.

As shown in FIG. 8C, in another embodiment, the substrate element 416 may comprise a laminated structure which includes a first layer 483 attached to a second layer 485. The substrate element 416 may further comprise a first zone 480, a second zone 481, and a weakened zone 482 disposed between the first zone 480 and the second zone 481. In some embodiments, the weakened zone 482 may comprise a discontinuity 470 in the first layer 483 such that a first zone thickness 463 and a second zone thickness 461 are each greater than at least part of a weakened zone thickness 465.

The cut line 423 can be positioned on the substrate element 416 such that the retaining element 404 comprises a substantial part of the weakened zone 482. As shown, the weakened zone 482 can be proximate to the single plane hinge line 422. When the single plane hinge line 422 is disposed proximate to the weakened zone 482, the weakened zone thickness 465 can allow part of the retaining element 404 to lift away from the first surface 417 of the substrate element 416.

The weakened zone thickness 465 can vary greatly. For example, the weakened zone thickness 465 can be less than or equal to about 75% of the first zone thickness 463 and/or the second zone thickness 461. As another example, the weakened zone thickness 465 can be less than or equal to about 50% of the first zone thickness 463 and/or the second zone thickness 461. As yet another example, the weakened zone thickness 465 can be less than or equal to about 25% of the first zone thickness 463 and/or the second zone thickness 461.

In other embodiments, the weakened zone 482 can be created by utilizing a substrate element 416 which has a varying basis weight. For example, the basis weight of the first layer 483, the second layer 485, or both, can vary in the weakened zone 482 such that there is less material in the weakened zone 482 as opposed to the material present in the first zone 480 and/or the second zone 481. In yet another embodiment, the basis weight of the first layer 483, the second layer 485, or both, can vary in the first zone 480 and/or the second zone 481 such that amount of material available in the first zone 480 and/or the second zone 481 is each greater than the material available in the weakened zone 482.

In some embodiments, the basis weight of the substrate element 416 in the weakened zone 482 can be less than about 25% of the basis weight of the first zone 480 and/or the second zone 481. In another embodiment, the basis weight of the weakened zone 482 can be less than about 50% of the basis weight of the first zone 480 and/or the second zone 481. In yet another embodiment, the basis weight of the weakened zone 482 can be less than about 75% of the basis weight of the first zone 480 and/or the second zone 481, or any individual number less than 75%.

The first fastening member 402, as discussed above, can be a composite including more than one layer of material or may be formed from a single layer of material. Where the first fastening member 402 includes the first layer 483 and the second layer 485, the first layer 483 or the second layer 485 may be a flexible material that would otherwise be insufficiently rigid to perform as a first fastening member but might provide desirable tactiles or aesthetics. In contrast, in some embodiments, the first layer 483 or the second layer 485 may comprise a more rigid material with suitable stiffness to perform as a retaining element and withstand expected forces when fastened to the second fastening member.

The variation of thicknesses as discussed above and/or the variation in basis weight of the substrate element 416 is equally applicable to the multiplane hinged fastening members discussed heretofore. However, because the retaining elements of the multiplane hinged fastening members are not cut out from the substrate element 416, the variation in thickness and/or basis weight can occur in either the substrate element or the retaining element of the multiplane hinged fastening members.

The fastening system 100 (shown in FIGS. 1A-1E) of the present invention can be made up of many different materials depending on the use of the fastening system 100 (shown in FIGS. 1A-1E). For example, the first fastening members discussed herein may be made from any suitable material and can be of any size and/or shape. The shape of the first fastening member will often be dependent on the end use of the fastening system 100 (shown in FIGS. 1A-1E), but in any case should be aesthetically pleasing, easy to hold and maneuver, and capable of maintaining a fastened configuration throughout the intended period of use when subjected to expected forces and external conditions.

The materials which make up the first fastening member should also be chosen depending on the end use of the fastening system 100 (shown in FIGS. 1A-1E). For example, if the fastening system 100 (shown in FIGS. 1A-1E) is to be used in a diaper, the first fastening member may include any material suitable for such a use, including but not limited to plastics, films, foams, nonwoven webs, woven webs, paper, laminates, steel, metals, foils, alloys, fiber reinforced plastics and the like, or combinations thereof. In embodiments where the fastening system 100 (shown in FIGS. 1A-1E) is used near or against the skin of a human or animal, the materials making up the first fastening member can be flexible. The flexibility allows the fastening system to conform to the shape of the body and thus, reduces the likelihood that the fastening system 100 (shown in FIGS. 1A-1E) will irritate or injure the wearer's skin.

The first fastening member may include one or more retaining elements. If the first fastening member includes more than one retaining element, the retaining elements can be operatively associated with each other such that they generally function as a single retaining element. Where the first fastening member comprises a plurality of retaining elements which generally functions as a single retaining element, the complexity of the fastening system 100 (shown in FIGS. 1A-1E) is reduced and it ensures that a single fastening motion can engage the first fastening member including the plurality of retaining elements. The use of a plurality of retaining elements in a first fastening member is discussed in U.S. Pat. No. 6,432,098.

The retaining elements described herein may be unitary with the substrate element or may be a separate element attached thereto. The retaining element may be attached to the substrate element at any location. Where the retaining element is separately attached to the substrate element, the retaining element may be made of the same or different materials than substrate element, making it easy to match the exact properties of the fastening system 100 (shown in FIGS. 1A-1E) to the intended use. Further, the material from which the retaining element is made can be reinforced and/or weakened at certain locations to help provide the desired flexibility and stiffness to the fastening system. In one embodiment the retaining element may be reinforced and/or weakened at one or both of its longitudinal ends 47A and 47B (shown in FIGS. 1A and 1C). In another embodiment, the retaining element may include a grip tab which may be reinforced and/or weakened. Exemplary methods of weakening the material of the retaining element include scoring, cutting, thinning, bending, heat treating, chemical treating and the like. Exemplary methods of reinforcing include heat or chemical treating the material, adding material, increasing the thickness and the like. The use of grip tabs in the first fastening member is discussed in U.S. Pat. No. 6,432,098.

In some embodiments, the retaining elements described herein may comprise a compressible material. The compressible material can be oriented such that the retaining element can be compressed in a direction generally parallel to the first longitudinal axis 15 (shown in FIGS. 1A-1C) and/or in a direction generally parallel to the first lateral axis 17 (shown in FIGS. 1A-1E and 7A-7G) and/or in a direction generally parallel to the first transverse axis 19 (shown in FIGS. 1A-1C). The compressible material can be oriented such that the retaining element can pass through the elongated opening in both the first orientation and the second orientation. For example, where the length S of the elongated opening 46 (shown in FIGS. 1A-1E, 2, 3A-3E, 4A-4D, 5, and 6) is less than the retaining element length R (shown in FIG. 1A), the retaining element 104 (shown in FIGS. 1A-1E, and 7A-7G) can be compressed in a direction generally parallel to the first longitudinal axis 15 (shown in FIGS. 1A-1C). In this example, compressing the retaining element 104 (shown in FIGS. 1A-1E, and 7A-7G) in a direction generally parallel to the first longitudinal axis 15 (shown in FIGS. 1A-1C) can allow the retaining element 104 to pass through the elongated opening 46 (shown in FIGS. 1A-1E, 2, 3A-3E, 4A-4D, 5, and 6) when the retaining element 104 is in the first orientation. After passing through the elongated opening 46 (shown in FIGS. 1A-1E, 2, 3A-3E, 4A-4D, 5, and 6) the compressible material of the retaining element can expand back into its un-compressed shape, thereby reducing the likelihood that the retaining element passes back through the elongated opening 46 (shown in FIGS. 1A-1E, 2, 3A-3E, 4A-4D, 5, and 6) unintentionally.

Any suitable compressible material can be used in the retaining elements and/or second fastening members. Some examples of suitable compressible materials include open cell foams, closed cell foams, elastics, rubber, inflatable bladders, corrugated materials, fluted materials, and the like.

The first fastening member may also include a secondary fastening element which provides a different means for fastening the components of the fastening system 100 (shown in FIGS. 1A-1E) to each other. For example, the first fastening member may include secondary fastening element located adjacent the distal edge of the retaining element or adjacent a grip tab, e.g. the intersecting region of the retaining element, distal edge of the retaining element. The secondary fastening element can be used to provide the closure system with the ability to better resist shear or peel forces, greater adjustability or other properties. Further, the secondary fastening element may provide the user with a means for fastening the article in a disposal configuration. The secondary fastening element can be any fastening means such as hooks, loops, adhesive, cohesive, magnetic materials, static electricity, snaps and the like or any combination of these or other known fastening means.

Similarly, the second fastening members discussed herein may be of any size and/or shape and may be made from any suitable material. As with the first fastening member, the shape of the second fastening member and the materials which make up the second fastening member will be dependent on the end use of the fastening system 100 (shown in FIGS. 1A-1E). For example, in end uses such as diapers, the second fastening member should be designed to be skin friendly, i.e. not harmful to the wearer's skin. Thus, it may be desirable to round the edges of the fastening system 100 (shown in FIGS. 1A-1E) and to size the elongated opening 46 (shown in FIGS. 1A-1E, 2, 3A-3E, 4A-4D, 5, and 6) so as to minimize the likelihood that skin will be caught in the fastening system. One way of minimizing the risk is to work the edges of the elongated opening 46 (shown in FIGS. 1A-1E, 2, 3A-3E, 4A-4D, 5, and 6) such that they are not sharp. Another way to make the fastening system 100 (shown in FIGS. 1A-1E) more skin friendly includes minimizing the thickness of the second fastening member (e.g. less than about 0.05 inches) or to design the first fastening member or the second fastening member such that the elongated opening 46 (shown in FIGS. 1A-1E, 2, 3A-3E, 4A-4D, 5, and 6) is filled in when the fastening device is closed. One more way is to provide a soft or compressible material on at least the surface of the fastening system 100 (shown in FIGS. 1A-1E) which faces the wearer.

The second fastening member may be made of materials the same as or different from the first fastening member including plastics, films, foams, nonwoven webs, woven webs, paper, laminates, steel, fiber reinforced plastics and the like, or combinations thereof. For example, in some embodiments, the second fastening member may comprise a compressible material. The compressible material of the second fastening member can be compressed, thereby allowing the retaining element to pass through the elongated opening while the retaining element is in the first orientation or the second orientation. The second fastening member can subsequently expand such that the retaining element cannot pass back through the elongated opening unintentionally.

While the second fastening member may be compressible, the second fastening member should be stiff enough in a direction parallel to the second lateral axis 21 (FIGS. 1A-1E) so as not to deform and let the retaining element of the first fastening member unintentionally disengage under expected use forces. The material from which the second fastening member is made can be reinforced or weakened at certain locations to help provide the desired flexibility and stiffness to the fastening device. In one embodiment the second fastening member may be reinforced and/or weakened at one or both of its longitudinal ends.

The second fastening member may also include a secondary fastening element which provides a different means for fastening the components of the fastening system to each other. For example, the second fastening member may include the secondary fastening element located adjacent the inboard portion, the outboard portion, a grip portion, or any other part of the second fastening member. As noted with regard to the first fastening member, the secondary fastening element can be used to provide the fastening system with the ability to better resist shear or peel forces, greater adjustability, a disposal feature and/or other features. The secondary fastening element can be any known fastening means such those described hereinbefore and may function together with or independently of any secondary fastening element disposed on the first fastening member. Secondary fastening elements and grip tabs are discussed in U.S. Patent Application Publication No. 2003/0233082.

The first fastening member and the second fastening member may comprise a tab and slot fastening system. For example, the first fastening member may comprise a tab member while the second fastening member comprises a slot member. Tab and slot fastening systems as well as tab members and slot members are discussed in U.S. Pat. No. 6,432,098 and in U.S. Patent Application Publication No. 2003/0233082.

The fastening system 100 (shown in FIGS. 1A-1C) of the present invention can be utilized in a number of different articles. For example, the fastening system 100 (shown in FIGS. 1A-1E) can be utilized in disposable absorbent articles such as disposable diapers, pull-on diaper, sanitary napkins, bibs, wipes, bandages, wraps, and the like. Exemplary articles are described in U.S. Pat. No. 6,432,098 and in U.S. Patent Application Publication No. 2003/0233082 A1. An exemplary use of the fastening system of the present invention is provided in FIG. 9.

Figure 9:
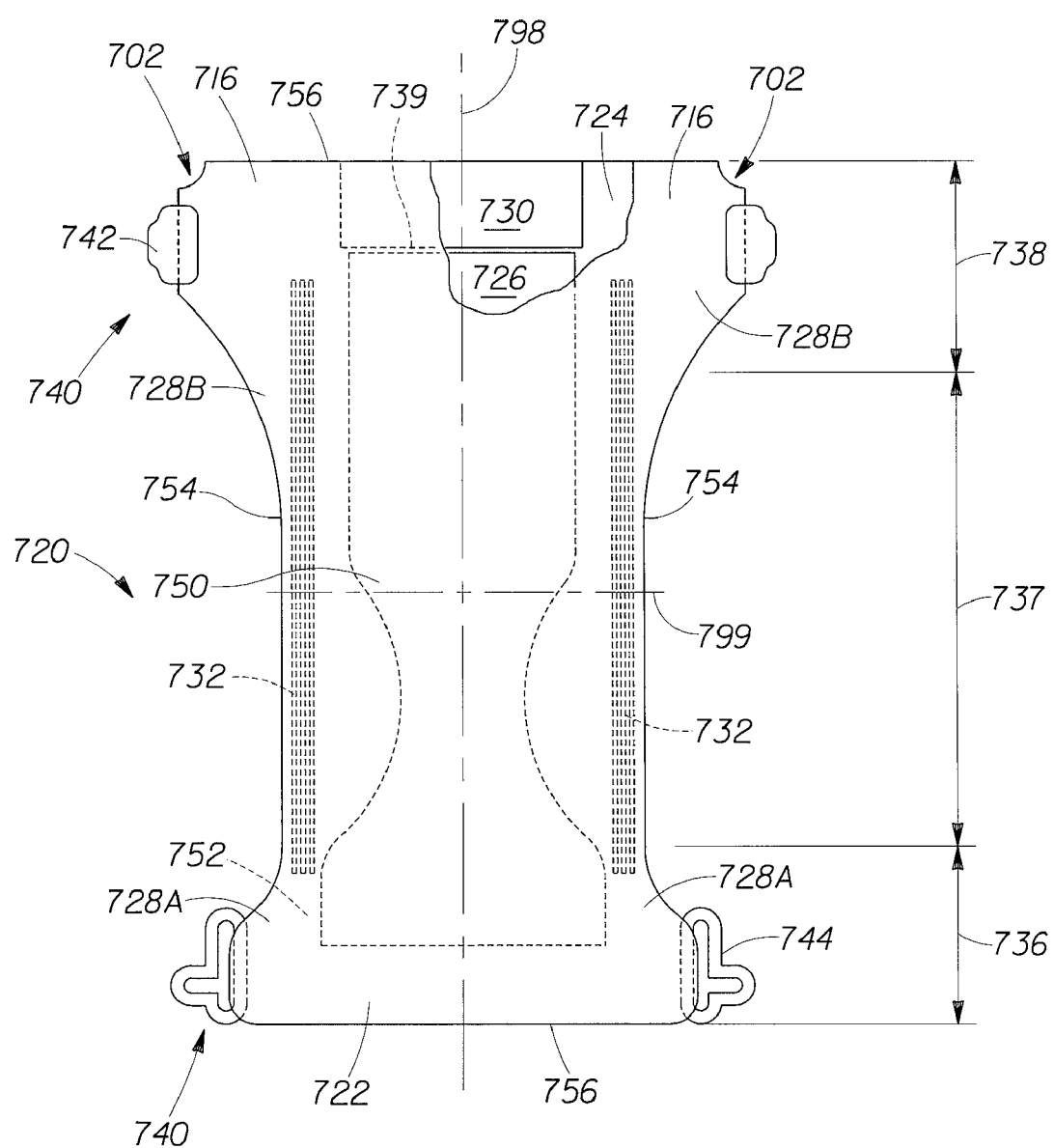
FIG. 9 is a partial cut-away view showing a disposable absorbent article constructed in accordance with the present invention. The disposable absorbent article is shown in a flat, uncontracted state (i.e., without elastic induced contraction).

As shown FIG. 9, a fastening system constructed in accordance with the present invention can be utilized in a disposable absorbent article 720 such as a diaper, for example. As shown, the fastening system comprises a tab member 702 and a slot member 744. As shown, the disposable absorbent article 720 is in its flat-out, uncontracted state (i.e., with elastic induced contraction pulled out) with parts of the structure being cut-away to more clearly show the construction of the disposable absorbent article 720. The portion of the disposable absorbent article 720 which faces or contacts the wearer, the inner surface 750, is oriented towards the viewer. The disposable absorbent article 720 may comprise a liquid pervious topsheet 722 and a backsheet 724 attached to at least a portion of the topsheet 722. The disposable absorbent article 720 further comprises an absorbent core 726 positioned between the topsheet 722 and the backsheet 724. The disposable absorbent article 720 may further comprise leg cuffs 732, a waist feature 730, a first pair of side panels 728A, and a second pair of side panels 728B.

The disposable absorbent article 720 is shown in FIG. 9 to have an outer surface 752 opposed to the inner surface 750, a first waist region 736, a second waist region 738 opposed to the first waist region 736, a crotch region 737 positioned between the first waist region 736 and the second waist region 738. The disposable absorbent article 720 also has longitudinal edges 754 and end edges 756. The longitudinal edges 754 generally run parallel to a longitudinal centerline 798, and the end edge 756 generally run parallel to a lateral centerline 799. The first pair of side panels 728A can extend outward from the disposable absorbent article 720 in the first waist region 736. The second pair of side panels 728B can extend outward from the disposable absorbent article 720 in the second waist region 738.

In some embodiments, the elastic waist feature 730 can extend longitudinally outward from at least one of the waist edges 739 of the absorbent core 726 and can form at least a portion of the end edge 756 of the disposable absorbent article 720. Examples of suitable waist features include those described in U.S. Pat. Nos. 4,515,595, 5,151,092, and 5,221,274. Although disposable diapers are generally constructed so as to have two elastic waist features, one positioned in a first waist region and one positioned in a second waist region, diapers can be constructed with a single elastic waist feature as shown in FIG. 9.

The disposable absorbent article 720 further comprises a fastening system 740 which can join at least a portion of the first waist region 736 with at least a portion of the second waist region 738, preferably to form leg and waist openings. The fastening system 740 may comprise the tab member 702 and the slot member 744. As shown, the tab members 702 may comprise a tab element 742 attached to a substrate element 716. The tab element 742 can be configured similar to any retaining element described herein. The substrate element 716 can be attached to the tab element 742 along a line of attachment and attached to the disposable absorbent article 720 in the second waist region 738.

As shown, a substrate element 716 can be integral with the disposable absorbent article 720. In some embodiments, the first pair of side panels 728A may comprise the substrate element 716. Alternatively, the substrate element 716 can be an element separately attached to the disposable absorbent article 720 in the second waist region 738. Alternatively, the substrate elements 716 can be attached to the disposable absorbent article in the first waist region 736. The substrate elements 716 can be elastically extensible such that the tab members 702 can extend and contract, thereby providing a comfortable fit to a wearer.

The slot member 744 may be unitary with the disposable absorbent article 720 or may be a separate element joined thereto. Further, the slot member 744 may be joined to the disposable absorbent article 720 at any suitable location. As shown, in some embodiments, the slot member 744 can be disposed in the first waist region 736 and attached to the second pair of side panels 728B. The slot member 744 can be configured similar to any second fastening member described herein.

The fastening system 740 can be prefastened such that a caregiver or wearer may pull on the disposable absorbent article 720 when removed from a package. Alternatively, the fastening system 740 can be unfastened in the package such that the caregiver or wearer fastens the fastening system while donning the disposable absorbent article 720. In yet another embodiment, a package may comprise both prefastened and unfastened disposable absorbent articles 720 for the convenience of the caregiver or the wearer.

The topsheet 722 and the backsheet 724 can have length and width dimensions generally larger than those of the absorbent core 726. While the topsheet 722, the backsheet 724, and the absorbent core 726, may include many different materials and may be assembled in a variety of well known configurations, exemplary diaper materials and configurations are described generally in U.S. Pat. Nos. 3,860,003; 5,151,092; and 5,221,274.

Some examples of suitable topsheets are described further in U.S. Pat. Nos. 3,929,135; 4,324,246; 4,342,314; 4,463, 045; 5,006,394; 4,609,518; 4,629,643. Any portion of the topsheet may be coated with a lotion as is known in the art. Examples of suitable lotions include those described in U.S. Pat. Nos. 5,607,760; 5,609,587; 5,635,191; 5,643,588; 5,968, 025; 6,716,441; and PCT Publication No. WO 95/24173.

Further, the topsheet may be fully or partially elasticated or may be foreshortened so as to provide a void space between the topsheet and the absorbent core. Exemplary structures including elasticized or foreshortened topsheets are described in more detail in U.S. Pat. Nos. 4,892,536; 4,990,147; 5,037, 416; and 5,269,775.

A suitable backsheet for use in the disposable absorbent article of the present invention may be impervious to liquids (e.g., urine) and comprise a thin plastic film such as a thermoplastic film having a thickness, for example, of about 0.012 mm (0.5 mil) to about 0.051 mm (2.0 mils). Suitable backsheet films include those manufactured by Tredegar Corporation, based in Richmond, Va., and sold under the trade name CPC2 film. Other suitable backsheet materials may include breathable materials which permit vapors to escape from the pull-on garment while still preventing exudates from passing through the backsheet. Suitable breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097. Some exemplary breathable composite materials are described in greater detail in PCT Application No. WO 95/16746; U.S. Pat. Nos. 5,938,648; 5,865,823; and 5,571,096.

The backsheet, or any portion thereof, may be elastically extensible in one or more directions. In one embodiment, the backsheet may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518, 801. In alternate embodiments, the backsheet may comprise elastic films, foams, strands, or combinations of these or other suitable materials with nonwovens or synthetic films.

A suitable absorbent core for use in the present invention may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Suitable absorbent structures for use as the absorbent core are described in U.S. Pat. Nos. 4,610,678; 4,673,402; 4,834,735; 4,888,231; 5,137,537; 5,147,345; 5,342,338; 5,260,345; 5,387,207; and 5,625,222.

The backsheet may be attached to the topsheet, the absorbent core, or any other element of the disposable absorbent article by any attachment means known in the art. For example, the attachment means may include a uniform continuous layer of adhesive, a patterned layer of adhesive, or an array of separate lines, spirals, or spots of adhesive. Some suitable attachment means are disclosed in U.S. Pat. Nos. 4,573,986; 3,911,173; 4,785,996; and 4,842,666. Examples of suitable adhesives are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The disposable absorbent article 720 preferably further comprises leg cuffs 732 to improve containment of liquids and other body exudates. Each elasticized leg cuff may include several different embodiments for reducing the leakage of body exudates in the leg regions. (The leg cuff can also be referred to as leg bands, side flaps, barrier cuffs, or elastic cuffs.) Exemplary articles include leg cuffs are described in U.S. Pat. Nos. 3,860,003; 4,909,803; and 4,695,278.

In embodiments, for example, where the first fastening member and the second fastening member comprise soft, compliant materials, the fastening system of the present invention can offer another advantage over conventional fastening systems. The advantage is discussed in regard to FIGS. 10A and 10B.

Figure 10A:
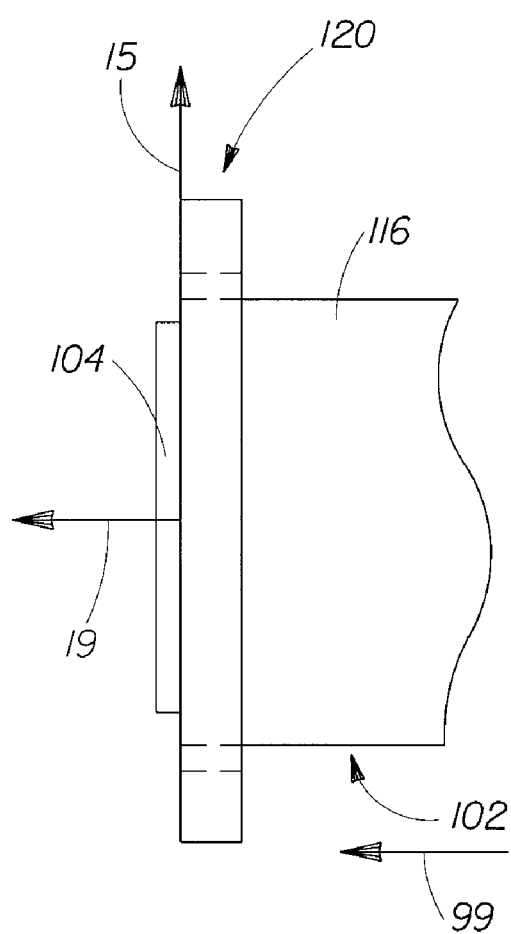
FIGS. 10A and 10B are elevation views showing the fastening system of FIG. 1A in a fastened state.
Figure 10B:
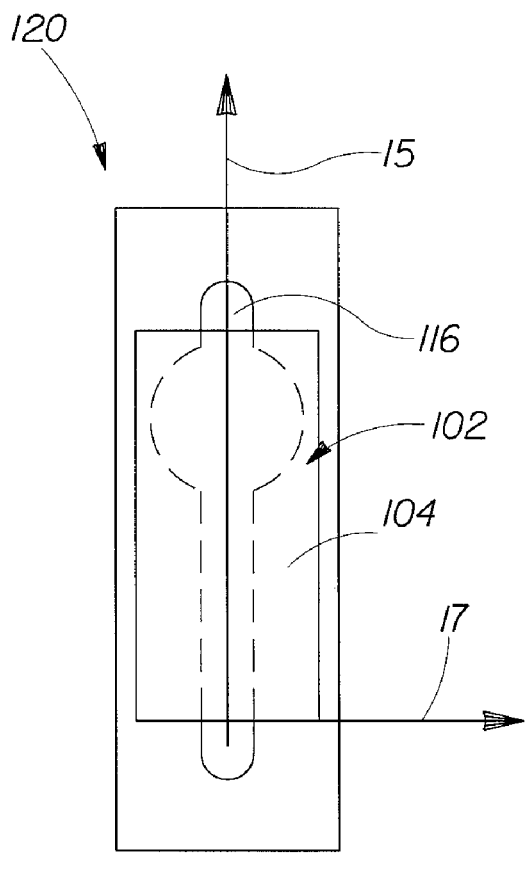

As shown in FIGS. 10A and 10B, another advantage of the fastening system of the present invention is that when fastened, the retaining element 104 can move relative to the second fastening member 120 without becoming unfastened, in some embodiments. As shown in FIG. 10A the first fastening member 102, including the retaining element 104 attached to the substrate element 116, is engaged with the second fastening member 120. As shown, in a fastened state, the first longitudinal axis 15 can be generally perpendicular to the engagement direction 99. Additionally, as shown, the first transverse axis 19 can be generally parallel to the engagement direction 99. In some embodiments, the retaining element 104 can move about 4 mm relative to the second fastening member 120 along the first longitudinal axis 15 and/or about 4 mm along the transverse axis 19 outward from the second fastening member 120 without the first fastening member 102 and the second fastening member 120 becoming unfastened.

As shown in FIG. 10B, in some embodiments, the retaining element 104 can move about 4 mm relative to the second fastening member 120 along the first lateral axis 17 without the first fastening member 102 and the second fastening member 120 becoming unfastened. In some embodiments, the retaining element 104 can move about 4 mm relative to the second fastening member 120 along the first longitudinal axis 15, along the first lateral axis 17, and along the first transverse axis 19 outward from the second fastening member 120, without the first fastening member 102 and the second fastening member 120 becoming unfastened.

Test Methods:

All measures to be carried out in temperature and humidity controlled conditions. Temperature is to be 22° C.+/−2° C. Relative Humidity is to be 50%+/−10%. All samples are to be held at these conditions for 24 hours prior to testing to allow them to equilibrate to the conditions.

Where the fastening systems are utilized in disposable absorbent articles, enough representative absorbent articles are selected from the retail packaging of the absorbent article to conduct all required tests. First fastening members and second fastening members are removed from the disposable absorbent articles by cutting via a pair of scissors.

Sample preparations for all measurements in the plan view for the first and second fastening members, samples should be prepared as follows.

1. Position the fastening member on a flat, level surface. There should be no external forces on the fastening member other than the force of gravity. The fastening member should not be compressed, bent, deflected, or changed from its natural, relaxed state.
2. Measure all distances to the nearest 0.25 mm. Any measurement device that is calibrated to measure accurately and precisely to 0.25 mm may be used, such as a standard metric (SI) ruler that is graduated in millimeters, a set of calipers, or an image analysis technique.
3.

Line of Attachment Length Compared to Retaining Element Length:

1. Measure the retaining element length R (shown in FIG. 1A). The retaining element length R is defined in the specification.
2. Measure the line of attachment length 1510 (shown in FIG. 1A). The line of attachment length 1510 is the maximum linear distance between two longitudinally outermost points on the line of attachment 72 (shown in FIG. 1A). A first point is longitudinally closer to the first longitudinal end 47A (shown in FIGS. 1A and 1C) than a second point, and the second point is longitudinally closer to the second longitudinal end 47B (shown in FIGS. 1A and 1C) than the first point. The line of attachment length 1510 is generally parallel to the first longitudinal axis 15 (shown in FIGS. 1A-1D).
3. Calculate the percentage of the line of attachment length 1510 to the retaining element length R, i.e. ((line of attachment length 1510/retaining element length R)*100)=percentage.

Retaining Element Length Compared to the Substrate Element Length:

1. Measure the retaining element length R (shown in FIG. 1A). The retaining element length R is defined in the specification.
2. Measure the substrate element length 31 (shown in FIG. 1A). The substrate element length 31 is the maximum linear distance of the substrate element 116 which laterally coincides with line of attachment 72 and is generally parallel to a first longitudinal axis as is defined herein.
3. Calculate the percentage of the retaining element length R to the substrate element length 31, i.e. ((retaining element length R/substrate element length 31)*100)=percentage.

Orientation Angle:

1. Secure the second fastening member in a clamp. The clamp is positioned adjacent to a longitudinal end which is disposed most distant from the intersecting region of the second fastening member.
2. Place an image collecting device, such as a camera, in front of the secured second fastening member. The image collecting device is positioned to record the plan view surface that includes the second lateral axis and the second longitudinal axis at a distance of approximately 1 meter away from the second fastening member. The second longitudinal axis is directly centered with the line of sight of the image collecting device.
3. Hold a retaining element 104 in a second orientation as described herein, and begin inserting first longitudinal end 47A (shown in FIGS. 1A and 1C) into the elongated opening 46. Obtain an image of retaining element and the second fastening member as the first longitudinal end 47A crosses the threshold of the elongated opening 46.

4. Repeat step 3 inserting second longitudinal end 47B (shown in FIGS. 1A and 1C) into the elongated opening 46.
5. If retaining element 104 can be inserted into elongated opening 46 over a range of orientation angles (as may be possible, for example, with a generally circular intersection region as shown in FIG. 1C), steps 3 and 4 are repeated for a full range of possible orientation angles. Repeat steps 3 and 4 altering the orientation angle by 10.0 degrees until both the maximum and the minimum orientation angle have been recorded.
6. From the images obtained in steps 3-5, identify the second longitudinal axis 23 and first lateral axis 17. Measure the angle between the second longitudinal axis 23 and first lateral axis 17 within +1.0 degree and record as Orientation Angle. Any suitable device for measuring angles to +1.0 degree may be used, such as a protractor or calibrated computer program capable of image analysis (if images have been digitally captured).

Intersecting Region Angle:
1. Position a second fastening member on a flat, level surface. There should be no external forces on the fastening member other than the force of gravity. The fastening member should not be compressed, bent, deflected or changed from its natural, relaxed state.
2. Identify the second longitudinal axis 23 (shown in FIGS. 1A-1E, 2, 3E, 4B, and 4C) and angular axis 612 (shown in FIGS. 4B and 4C) as described herein.
3. Measure the angle between the second longitudinal axis 23 and angular axis 612 within +1.0 degree and record as Intersection Region Angle 630. Any suitable device for measuring angles to +1.0 degree may be used, such as a protractor or calibrated computer program capable of image analysis (if images have been digitally captured).

Thickness of Substrate Element and/or Retaining Element
The cross sectional heights of the substrate element and/or the retaining element are to be measured to the nearest 0.05 mm at an applied pressure which does not cause deformation of greater than 0.005 mm of the sample while being measured. Use a measuring device such as a Vernier caliper or micrometer that is calibrated to measure to the nearest 0.05 mm without causing deformation of the sample and is capable of measuring small areas.
 1. Measure thickness of a first zone, a second zone, and a weakened zone. The measurement includes all layers of the substrate element.
 Calculations follow:

Ratio of thicknesses, expressed as %=100*(thickness of weakened zone)/(thickness of first zone) OR Ratio of thicknesses, expressed as %=100*(thickness of weakened zone)/(thickness of second zone).

Method to Measure Basis Weight Variation
Basis Weight is mass per unit area and is to be measured in grams per square meter, to the nearest 1 gram/m$^2$.
 1. Basis weight is to be measured using any suitable method of determining mass per unit area. Suitable methods include EDANA 40.3-90. Smaller test areas may be used if needed to measure basis weight variations within the test sample (substrate element and/or tab element). In any case, a sample of known area is weighed. The result is determined by dividing the mass of the sample by the area of the sample. The fastening device should be measured sufficiently to determine basis weight variations in a lateral direction and a longitudinal direction of a test sample.
 2. Calculations follow:

Ratio of Basis Weights, expressed as %=100*(Basis Weight of weakened region)/(Basis Weight of first region).

Ratio of Basis Weights, expressed as %=100*(Basis Weight of weakened region)/(Basis Weight of second zone).

Figure 11A:
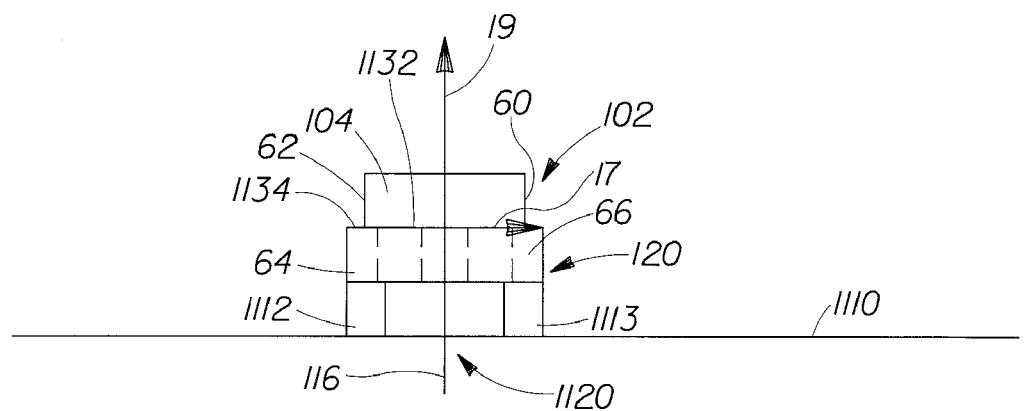
FIG. 11A is an elevation view showing a first fastening member and a second fastening member in a fastened state disposed on a level surface.
Figure 11B:
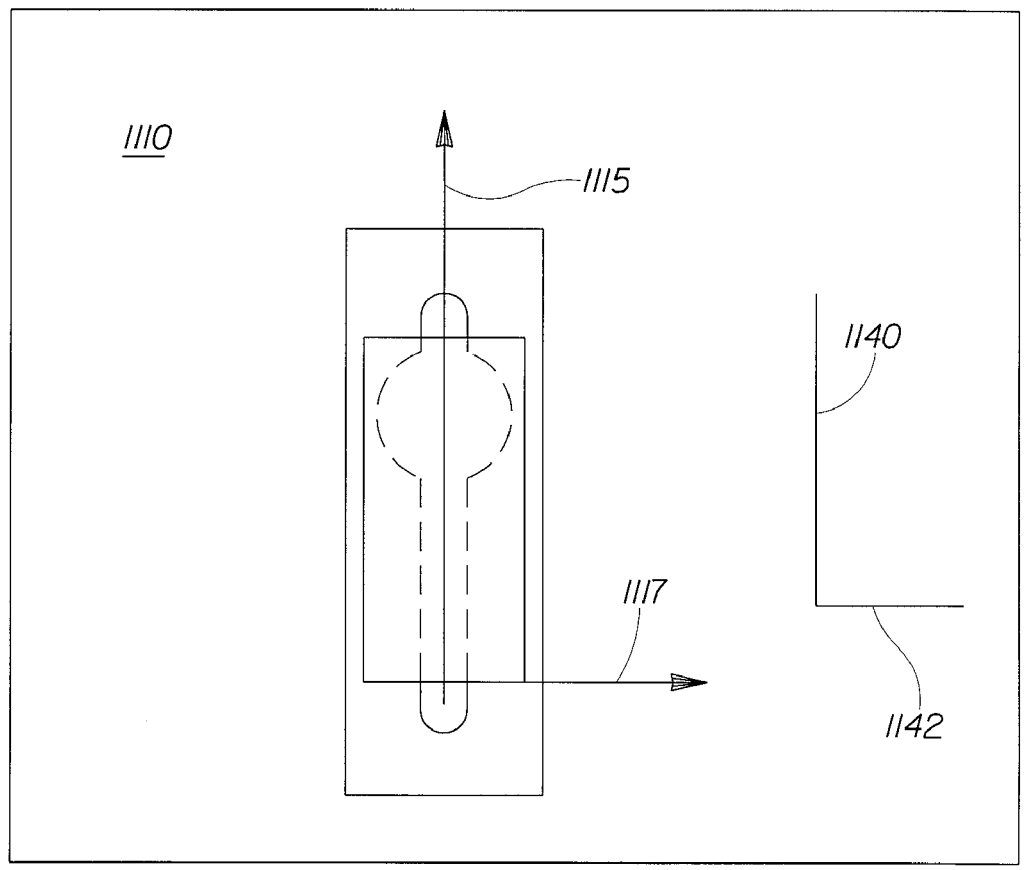
FIG. 11B is a plan view showing the first fastening member and the second fastening member of FIG. 11A.

Relative Movement of Retaining Element to the Second Fastening Member
Measure all distances to the nearest 0.25 mm. Any measurement device that is calibrated to measure accurately & precisely to 0.25 mm may be used, such as a standard metric (SI) ruler that is graduated in millimeters, a set of calipers, or an image analysis technique.
1. As shown in FIG. 11A, fasten the first fastening member 102 and the second fastening member 120 and position the connected fastening members on a flat, level surface 1110. The second fastening member 120 is positioned between the first fastening member 102 and the level surface 1110. The level surface 1110 has an opening 1120 which allows the substrate element 116 to pass therethrough and hang in a vertical orientation. No external forces are applied on the fastening members other than the force of gravity. The fastening members are in a relaxed state.
2. Secure the inboard portion 64 and the outboard portion 66 of the second fastening member 120 to the level surface 1110 via a double sided tape 1112 and 1113. The second fastening member 120 is secured without restricting the movement of the first fastening member 102. Suitable double sided tape is available from Avery Dennison Corp., Painesville, Ohio, under the supplier code of FT 239.
3. Apply a uniform load of 5 grams/mm (where normalizing distance in millimeters corresponds to retaining element length R) across the retaining element length R in a direction outward from the second fastening member 120 parallel to the first transverse axis 19.
4. Measure the distance between a surface 1132 of the retaining element and a surface 1134 of the second fastening member 120. The distance is the maximum linear distance parallel to the first transverse axis 19.
5. Remove the uniform load of step 3 and return the first fastening member 102 to its original position.
6. As shown in FIG. 11B, draw a first reference line 1140 on the level surface 1110 parallel to the first longitudinal axis 15. Draw a second reference line 1142 on the level surface 1110 parallel to the first lateral axis 17. Both the first and the second reference lines 1140 and 1142 are placed on the level surface 1110 such that they are visible after movement of the retaining element 104.
7. Draw a third reference line 1115 on the first fastening member 102 parallel to the first longitudinal axis 15. Draw a fourth reference line 1117 on the first fastening member 102 parallel to the first lateral axis 17.
8. Measure a first initial distance between the first reference line 1140 and the third reference line 1115. The first initial distance is the maximum linear distance parallel to the first lateral axis 17. Measure a second initial distance between the second reference line 1142 and the fourth reference line 1117. The second initial distance is the maximum linear distance parallel to the first longitudinal axis 15.
9. Apply a uniform load of 5 grams/mm (where normalizing distance in millimeters corresponds to retaining element length R) across the distal edge 62 of retaining element 104 in a direction generally parallel to the first lateral axis 17.

10. Measure a first final distance from the first reference line 1140 to the third reference line 1115. The first final distance is the maximum linear distance parallel to the first lateral axis 17.
11. Calculate the difference between the first initial distance and first final distance, thereby determining a first lateral movement distance.
12. Remove the uniform load of step 9.
13. Apply a uniform load of 5 grams/mm (where normalizing distance in millimeters corresponds to retaining element length R) across the proximal edge 60 of retaining element 104 in a direction generally parallel to the first lateral axis 17.
14. Measure a second final distance from the first reference line 1140 to the third reference line 1115. The second final distance is the maximum linear distance parallel to the first lateral axis 17.
15. Calculate the difference between the first initial distance and second final distance, thereby determining a second lateral movement distance.
16. Calculate the movement of the retaining element 104 with respect to the second fastening member 120 by adding the first lateral movement distance and the second lateral movement distance.
17. Remove the applied load of step 13 and return the first fastening member 102 to its original position.
18. Apply a uniform load of 5 grams/mm (where normalizing distance in millimeters corresponds to retaining element length R) across the first longitudinal end 47A of retaining element 104 in a direction generally parallel to first longitudinal axis 15 (shown in FIG. 1A).
19. Measure a third final distance from the second reference line 1142 to the fourth reference line 1117. The third final distance is the maximum linear distance parallel to the first longitudinal axis 15 (shown in FIG. 1A).
20. Calculate the difference between the second initial distance and the third final distance, thereby determining a first longitudinal movement distance.
21. Remove the uniform load of step 9.
22. Apply a uniform load of 5 grams/mm (where normalizing distance in millimeters corresponds to retaining element length R) across the second longitudinal end 47B of retaining element 104 in a direction generally parallel to the first longitudinal axis 15 (shown in FIG. 1A).
23. Measure a fourth final distance from the second reference line 1140 to the fourth reference line 1117. The fourth final distance is the maximum linear distance parallel to the first longitudinal axis 15.
24. Calculate the difference between the second initial distance and fourth final distance, thereby determining a second longitudinal movement distance.
25. Calculate the movement of the retaining element 104 with respect to the second fastening member 120 by adding the first longitudinal movement distance and the second longitudinal movement distance.
26. Remove the applied load of step 22.
End of Test Methods.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fastening system comprising:
   (a) a first fastening member including:
      (1) a substrate element; and
      (2) a retaining element attached to the substrate element along a line of attachment, the retaining element having a retaining element length; and
   (b) a second fastening member including:
      (1) an inboard portion; and
      (2) an outboard portion, wherein the inboard portion and the outboard portion define an elongated opening in the second fastening member, wherein the elongated opening includes a longitudinal axis, wherein the elongated opening has an elongated opening length, wherein the retaining element length is greater than about 25% of the elongated opening length, wherein the elongated opening includes a longitudinal region and an intersecting region, wherein the longitudinal region includes a longitudinal region width and the intersecting region includes an intersection region width, wherein the intersection region width is greater than the longitudinal width, and wherein at least part of the retaining element is capable of passing through the elongated opening and engaging the outboard portion of the second fastening member, thereby fastening the first fastening member and the second fastening member.

2. The fastening system of claim 1, wherein the retaining element length is greater than or equal to about 50% of the elongated opening length.

3. The fastening system of claim 1, wherein the retaining element comprises a tab element, and the second fastening member comprises a slot member, and wherein the elongated opening comprises a slot.

4. The fastening system of claim 1, wherein the intersection region width is greater than or equal to about 50% of a retaining element width.

5. The fastening system of claim 1, wherein the intersection region width is greater than or equal to about 75% of a retaining element width.

6. The fastening system of claim 1, wherein the intersection region width is greater than or equal to about 100% of a retaining element width.

7. The fastening system of claim 1, wherein the intersecting region comprises a first area which extends outward from the elongated opening into the inboard portion of the second fastening member.

8. The fastening system of claim 7, wherein the first area comprises a first area length which is less than about 25% of an elongated opening length.

9. The fastening system of claim 7, wherein the intersecting region further comprises a second area which extends outward from the elongated opening into the outboard portion of the second fastening member.

10. The fastening system of claim 9, wherein the first area comprises a first area length and the second area comprises a second area length, wherein each of the first area length and the second area length are less than about 75% of an elongated opening length.

11. The fastening system of claim 1, wherein the intersecting region comprises a second area which extends outward from the elongated opening into the outboard portion of the second fastening member.

12. The fastening system of claim 1, wherein the intersecting region comprises a first area which extends outward from elongated opening and into the inboard portion of the second fastening member, wherein the intersecting region further comprises an angular axis, and wherein an angle between the longitudinal axis of the elongated opening and the angular axis is greater than or equal to about 0 degrees to less than or equal to about 180 degrees.

* * * * *